US010202423B2

(12) United States Patent
D'Aoust et al.

(10) Patent No.: US 10,202,423 B2
(45) Date of Patent: Feb. 12, 2019

(54) PICORNAVIRUS-LIKE PARTICLE PRODUCTION IN PLANTS

(71) Applicant: MEDICAGO INC., Quebec (CA)

(72) Inventors: Marc-Andre D'Aoust, Quebec (CA); Pierre-Olivier Lavoie, Quebec (CA); Manon Couture, St. Augustin de Desmaures (CA); Lucie Poulin, Quebec (CA); Louis-Philippe Vezina, Quebec (CA)

(73) Assignee: Medicago Inc. of Quebec, Canada, Quebec (CA)

( * ) Notice: Subject to any disclaimer, the term of this patent is extended or adjusted under 35 U.S.C. 154(b) by 260 days.

(21) Appl. No.: 14/426,019

(22) PCT Filed: Aug. 29, 2013

(86) PCT No.: PCT/CA2013/050666

§ 371 (c)(1),
(2) Date: Mar. 4, 2015

(87) PCT Pub. No.: WO2014/036645

PCT Pub. Date: Mar. 13, 2014

(65) Prior Publication Data

US 2015/0225462 A1 Aug. 13, 2015

Related U.S. Application Data

(60) Provisional application No. 61/697,266, filed on Sep. 5, 2012.

(51) Int. Cl.

| | |
|---|---|
| ***C07K 14/00*** | (2006.01) |
| ***C07K 14/005*** | (2006.01) |

(Continued)

(52) U.S. Cl.

CPC .......... *C07K 14/005* (2013.01); *A61K 39/125* (2013.01); *A61K 39/13* (2013.01);

(Continued)

(58) Field of Classification Search

None

See application file for complete search history.

(56) References Cited

U.S. PATENT DOCUMENTS

| | | | |
|---|---|---|---|
| 6,110,466 A | 8/2000 | Lomonossoff et al. | |
| 6,392,121 B1 * | 5/2002 | Mason ............... | C12N 15/8203 435/235.1 |

(Continued)

FOREIGN PATENT DOCUMENTS

| | | |
|---|---|---|
| WO | WO 2008/016594 | 2/2008 |
| WO | WO 2009/009876 | 1/2009 |

(Continued)

OTHER PUBLICATIONS

Hu et al. Formation of enterovirus-like particle aggregates by recombinant baculoviruses co-expressing P1 and 3CD in insect cells. Biotechnology Letters. Jun. 2003, vol. 25, Issue 12, pp. 919-925.*

(Continued)

*Primary Examiner* — Michelle S Horning

(74) *Attorney, Agent, or Firm* — Kenneth H. Sonnenfeld; Nicole Fortune; King & Spalding LLP

(57) ABSTRACT

A method of producing a picornavirus-like particle (PVLP) in a plant is provided. The method comprises introducing a first nucleic acid and a second nucleic acid into the plant, portion of the plant, or a plant cell. The first nucleic acid comprising a first regulatory region active in the plant operatively linked to a nucleotide sequence encoding a polyprotein. The second nucleic acid comprises a second regulatory region active in the plant and operatively linked (Continued)

to a nucleotide sequence encoding one or more protease. The plant, portion of the plant, or plant cell is incubated under conditions that permit the expression of the nucleic acids, thereby producing the PVLP. A PVLP comprising the polyprotein is also provided.

17 Claims, 14 Drawing Sheets

Specification includes a Sequence Listing.

(51) Int. Cl.
*C07K 16/10* (2006.01)
*C12N 15/82* (2006.01)
*A61K 39/125* (2006.01)
*A61K 39/13* (2006.01)
*C12N 7/00* (2006.01)

(52) U.S. Cl.
CPC ............ *C07K 16/1009* (2013.01); *C12N 7/00* (2013.01); *C12N 15/8258* (2013.01); *C07K 2317/10* (2013.01); *C12N 2770/32322* (2013.01); *C12N 2770/32323* (2013.01); *C12N 2770/32351* (2013.01); *C12N 2770/32623* (2013.01); *C12N 2770/32634* (2013.01); *C12N 2800/22* (2013.01)

(56) References Cited

U.S. PATENT DOCUMENTS 8,674,084 B2* 3/2014 Sainsbury .......... C12N 15/8203 435/320.1
2010/0125918 A1 5/2010 Chen et al.
2011/0262966 A1 10/2011 Mason et al.
2013/0295609 A1* 11/2013 D'Aoust ............ C12N 15/8203 435/69.3

FOREIGN PATENT DOCUMENTS

WO WO 2010/003225 1/2010
WO WO 2010/025285 3/2010
WO WO 2011/048353 4/2011
WO WO 2011/112945 9/2011
WO WO 2012/058762 5/2012

OTHER PUBLICATIONS

D'Aoust, et al., "The Production of Hemagglutinin-Based Virus-Like Particles in Plants: A Rapid, Efficient and Safe Response to Pandemic Influenza," Plant Biotech. J. 8, pp. 1-13, 2010.
Medicago Inc., Office Action for Canadian Patent Application No. 2,884,073, dated May 27, 2016, 4 pages.
Medicago Inc., Notice of Allowance for Canadian Patent Application No. 2,884,073, dated Sep. 15, 2016, 1 pages.
Medicago Inc., Office Action for Chinese Patent Application No. 201380055096.5, dated Jul. 11, 2016, 3 pages, (associate's translation).
Medicago Inc., Extended European Search Report for European Patent Application No. EP 13835101.0, dated May 30, 2016, 8 pages.
Medicago Inc., Communication pursuant to Rules 70(2) and 70a(2) EPC for European Patent Application No. EP 13835101.0, dated Jun. 16, 2016, 1 page.
Medicago Inc., Written Opinion for Singapore Patent Application No. 11201501523X, dated May 16, 2016, 8 pages.
Medicago Inc., Search Report for Singapore Patent Application No. 11201501523X, dated May 13, 2016, 3 pages.
D.C. Ansardi et al., "Coinfection with recombinant vaccinia viruses expressing poliovirus P1 and P3 proteins results in polyprotein processing and formation of empty capsid structures", Journal of Virology, 65:4, pp. 2088-2092, 1991.
Hsuan-Fu Chen et al., "Oral immunization of mice using transgenic tomato fruit expressing VP1 protein from enterovirus 71", Vaccine 24, pp. 2944-2951, 2006.
Yao-Chi Chung et al., "Expression, purification and characterization of enterovirus-71 virus-like particles", World Journal of Gastroenterology, vol. 12:6, pp. 921-927, 2006.
Cheng-Yu Chung et al., "Enterovirus 71 virus-like particle vaccine: Improved production conditions for enhanced yield", Vaccine 28:43, pp. 6951-6957, 2010.
Yao-Chi Chung et al., "Immunization with virus-like particles of enterovirus 71 elicits potent immune responses and protects mice against lethal challenge", Vaccine, 26:15, pp. 1855-1862, 2008.
Elisa Crisci et al., "Virus-like particles: The new frontier of vaccines for animal viral infections", Veterinary Immunology and Immunopathology, pp. 1-15, 2012.
Maria J. Dus Santos et al., "Development of transgenic alfalfa plants containing the foot and mouth disease virus structural polyprotein gene P1 and its utilization as an experimental immunogen", Vaccine, vol. 23, pp. 1838-1843, 2005.
Yu-Chen Hu et al., "Formation of enterovirus-like particle aggregates by recombinant baculoviruses co-expressing P1 and 3CD in insect cells", Biotechnology Letters 25, pp. 919-925, 2003.
Yu-Li Lin et al., "Enterovirus type 71 neutralizing antibodies in the serum of macaque monkeys immunized with EV71 virus-like particles", Vaccine, 30:7, pp. 1305-1312, 2012.
Raffaele Lombardi et al., "High-level HIV-1 Nef transient expression in Nicotiana benthamiana using the P19 gene silencing suppressor protein of Artichoke Mottled Crinckle Virus", BMC Biotechnology, 9:96, pp. 1-11, 2009.
Li Pan et al., "Foliar extracts from transgenic tomato plants expressing the structural polyprotein, P1-2A, and protease, 3C, from foot-and-mouth disease virus elicit a protective response in guinea pigs", Veterinary Immunology and Immunopathology 121, pp. 83-90, 2008.
Claudine Porta et al., "Rational Engineering of Recombinant Picornavirus Capsids to Produce Safe, Protective Vaccine Antigen", PLOS Pathogens, 9:3, pp. 1-8, 2013.
Dingmei Zhang et al., "Enterovirus 71 vaccine: close but still far", International Journal of Infectious Diseases, 14:9, pp. 739-743, 2010.
Edward P. Rybicki, "Plant-made vaccines for humans and animals", Plant Biotechnology Journal, vol. 8, pp. 620-637, 2010.
Rainer Fischer et al., "Towards molecular farming in the future: transient protein expression in plants", Biotechnol. Appl. Biochem., 30, pp. 113-116, 1999.
Rainer Fischer et al., "Towards molecular farming in the future: moving from diagnostic protein and antibody production to microbes to plants", Biotechnol. Appl. Biochem., 30, pp. 101-108, 1999.
Examination Report, dated Apr. 9, 2015 in Canadian Patent Application No. 2,884,073 (national phase of PCT/CA2013/050666), (5 pages).
International Search Report and Written Opinion from corresponding PCT/CA2013/050666. dated Dec. 2, 2013 (15 pages).
International Preliminary Report on Patentability from corresponding PCT/CA2013/050666, dated Dec. 15, 2014 (12 pages).
Response to Written Opinion, Amendment under Article 14 of the PCT, from corresponding PCT/CA2013/050666, filed Jul. 4, 2014, (9 pages).
Applicant: Medicago Inc., Office Action in Canadian Patent Application No. 2,884,073, dated Sep. 24, 2015, 4 pages.
Applicant: Medicago Inc., Office Action in Canadian Patent Application No. 2,884,073, dated Jan. 7, 2016, 5 pages.
Chung et al., "Expression, purification and characterization of enterovirus-71 virus-like particles," World J Gastroenterol 12(6): 921-927, Feb. 14, 2006.
Bräutigam et al., "Formation of Poliovirus-like Particles by Recombinant Baculoviruses Expressing the Individual VP0, VP3, and VP1 Proteins by Comparison to Particles Derived from the Expressed Poliovirus Polyprotein," Virology, 192, pp. 512-524, 1993.

(56) References Cited

OTHER PUBLICATIONS

Liu et al., "Purification and Characterization of Enterovirus 71 Viral Particles Produced from Vero Cells Grown in a Serum-Free Microcarrier Bioreactor System," PlosOne, 6(5), E20005, pp. 1-9, 2011.
Xu, et al. "EV71: An Emerging infectious disease vaccine target in the Far East?" Vaccine, 2010 vol. 28:20, pp. 3516-3521.
Medicago Inc., English Translation of Office Action for Chinese Patent Application No. 201380055096.5, dated Jan. 9, 2017, 1 page.
Medicago Inc., Notification of Third Office Action for Chinese Patent Application No. 201380055096.5, dated Sep. 28, 2017, 12 pages.
Medicago Inc., Communication Pursuant to Article 94(3) EPC for European Patent Application No. 13 835 101.0, dated Jun. 19, 2017, 5 pages.
Medicago Inc., Communication Pursuant to Article 94(3) EPC for European Patent Application No. 13 835 101.0, dated Jan. 8, 2018, 5 pages.
Medicago Inc., Examination Report for New Zealand Patent Application No. 705488, dated Jun. 16, 2017, 3 pages.
Medicago Inc., Further Examination Report for New Zealand Patent Application No. 705488, dated Dec. 20, 2017, 5 pages.
Medicago Inc., Invitation to Response to Written Opinion for Singapore Patent Application No. 11201501523X, dated Aug. 16, 2017, 8 pages.
Medicago Inc., English Translation of Office Action for Russian Patent Application No. 2015109663, dated Jun. 16, 2017, 6 pages.
Medicago Inc., Notice of Reasons for Rejection for Japanese Patent Application No. 2015-528819, dated Jun. 21, 2017, 6 pages.
Wang et al. , "Duck hepatitis A virus structural proteins expressed in insect cells self-assembleinto virus-like particles with strong immunogenicity in ducklings" Veterinary Microbiology, 2018, vol. 215, pp. 23-28.

* cited by examiner

A.

B.

Figure 9A (SEQ ID NO: 1)

GPSLDFALSLLRRNVRQVQTDQGHFTMLGVRDRLAVLPRHSQPGKTIWIEHKLVNVLDA
VELVDEQGVNLELTLITLDTNEKFRDITKFIPENISAASDATLVINTEHMPSMFVPVGD
VVQYGFLNLSGKPTHRTMMYNFPTKAGQCGGVVTSVGKIIGIHIGGNGRQGFCAGLKRS
YFASEQGEIQWVKPNKETGRLNINGPTRTKLEPSVFHDIFEGNKEPAVLHSKDPRLEVD
FEQALFSKYVGNTLYEPDEYIKEAALHYANQLKQLEINTSQMSMEEACYGTENLEAIDL
HTSAGYPYSALGIKKRDILDPTTRDVSKMKFYMDKYGLDLPYSTYVKDELRSIDKIKKG
KSRLIEASSLNDSVYLRMAFGHLYEAFHANPGTITGSAVGCNPDTFWSKLPILLPGSLF
AFDYSGYDASLSPVWFRALELVLREIGYSEGAVSLIEGINHTHHVYRNKTYCVLGGMPS
GCSGTSIFNSMINNIIIRALLIKTFKGIDLDELNMVAYGDDVLASYPFPIDCLELAKTG
KEYGLTMTPADKSPCFNEVNWGNATFLKRGFLPDEQFPFLIHPTMPMREIHESIRWTKD
ARNTQDHVRSLCLLAWHNGKQEYEKFVSTIRSVPVGRALAIPNYENLRRNWLELF

Figure 9B (SEQ ID NO: 2)

GGCCCGAGCCTTGATTTTGCCCTCTCCCTACTGAGGAGGAACGTCAGGCAAGTCCAAAC
AGACCAGGGGCATTTCACCATGTTGGGTGTTAGGGATCGCTTAGCAGTCCTCCCACGCC
ACTCACAACCCGGCAAAACTATTTGGATTGAGCACAAACTCGTGAACGTCCTTGATGCA
GTTGAATTGGTGGATGAGCAAGGAGTCAACCTGGAGTTAACCCTCATCACTCTTGACAC
TAACGAAAAGTTTAGGGATATCACCAAATTCATCCCAGAAAATATTAGTGCTGCCAGTG
ATGCCACCCTAGTGATCAACACGGAGCACATGCCCTCAATGTTTGTCCCGGTGGGTGAC
GTTGTGCAGTATGGCTTCTTGAACCTCAGTGGCAAGCCTACCCATCGCACCATGATGTA
CAACTTTCCTACTAAAGCAGGACAGTGTGGGGGAGTGGTGACATCTGTTGGGAAGATTA
TCGGTATTCACATTGGTGGCAATGGCAGACAAGGTTTTTGCGCAGGCCTCAAAAGGAGT
TACTTTGCTAGTGAACAAGGAGAGATCCAGTGGGTTAAGCCCAATAAAGAAACTGGAAG
ACTCAACATCAATGGACCAACCCGCACCAAGCTAGAACCCAGTGTATTCCATGATATCT
TTGAGGGAAATAAGGAGCCAGCTGTCTTGCACAGTAAAGACCCCCGACTTGAGGTAGAT
TTTGAACAGGCCCTGTTCTCTAAGTATGTGGGGAATACACTATATGAGCCTGACGAGTA
CATCAAAGAGGCAGCTCTTCATTATGCAAACCAATTAAAGCAGCTAGAAATCAACACCT
CTCAAATGAGCATGGAGGAGGCCTGCTACGGTACTGAGAATCTTGAGGCTATTGATCTT
CATACTAGTGCAGGTTACCCCTATAGTGCCCTGGGGATAAAGAAAAGAGACATCTTAGA
CCCTACCACCAGGGACGTGAGTAAAATGAAGTTCTACATGGACAAATATGGTCTTGATC
TCCCTTACTCCACTTATGTCAAGGACGAGCTGCGCTCAATTGATAAAATTAAGAAAGGG
AAGTCCCGTCTGATTGAGGCCAGTAGTTTAAATGATTCAGTGTACCTTAGAATGGCTTT
CGGTCATTTGTATGAGGCTTTCCACGCAAATCCTGGGACTATAACTGGATCAGCCGTGG
GGTGTAACCCTGACACATTCTGGAGCAAGCTGCCAATTTTGCTCCCTGGTTCACTCTTT
GCCTTTGACTACTCAGGTTATGATGCTAGCCTTAGCCCTGTCTGGTTCAGAGCATTAGA
ATTGGTCCTTAGGGAGATAGGGTATAGTGAAGGGGCAGTCTCACTCATTGAGGGAATCA
ACCACACACACCATGTGTATCGTAATAAGACCTATTGTGTGCTTGGTGGGATGCCCTCA
GGCTGCTCGGGAACATCCATTTTCAACTCAATGATCAACAACATTATTATCAGAGCACT
GCTCATAAAAACATTTAAGGGCATTGATTTGGATGAACTCAACATGGTCGCTTATGGAG
ATGATGTGCTCGCTAGCTACCCCTTCCCAATTGATTGCTTGGAGTTAGCGAAGACTGGC
AAGGAGTATGGTCTAACCATGACCCCTGCGGATAAGTCTCCTTGCTTTAATGAAGTTAA
TTGGGGTAATGCGACCTTTCTCAAGAGGGGCTTTTTACCCGATGAACAGTTTCCATTTT
TGATCCACCCCACTATGCCAATGAGGGAGATCCATGAGTCCATTCGATGGACCAAGGAT
GCACGAAACACTCAAGATCATGTGCGGTCCTTGTGCCTCCTAGCATGGCATAATGGTAA

TO FIG. 9B (cont.)

FROM FIG. 9B

Figure 9B (cont.)

GCAAGAATATGAGAAATTTGTGAGTACAATTAGGTCTGTCCCAGTGGGAAGAGCGTTGG
CTATCCCAAATTATGAAAACCTTAGACGTAATTGGCTCGAGTTATTT

Figure 9C (SEQ ID NO: 3)

GPSLDFALSLLRRNIRQVQTDQGHFTMLGVRDRLAVLPRHSQPGKTIWIEHKLVNILDA
VELVDEQGVNLELTLITLDTNEKFRDITKFIPESISTASDATLVINTEHMPSMFVPVGD
VVQYGFLNLSGKPTHRTMMYNFPTKAGQCGGVVTSVGKVIGIHIGGNGRQGFCAGLKRS
YFASEQGEIQWVKPNKETGRLNINGPTRTKLEPSVFHDVFEGNKEPAVLHGKDPRLEVD
FEQALFSKYVGNTLYEPDEYIKEAALHYANQLKQLEINTSQMSMEEACYGTENLEAIDL
HTSAGYPYSALGIKKRDILDPTTRDVSKMKSYMDKYGLDLPYSTYVKDELRSIDKIKKG
KSRLIEASSLNDSVYLRMTFGHLYEAFHANPGTITGSAVGCNPDTFWSKLPILLPGSLF
AFDYSGYDASLSPVWFRALEMVLREIGYSEEAVSLIEGINHTHHVYRNKTYCVLGGMPS
GCSGTSIFNSMINNIIIRALLIKTFKGIDLDELNMVAYGDDVLASYPFPIDCLELAKTG
KEYGLTMTPADKSPCFNEVNWGNATFLKRGFLPDEQFPFLIHPTMPMREIHESIRWTKD
ARNTQDHVRSLCLLAWHNGKQEYEKFVSTIRSVPIGRALAIPNYENLRRNWLELF

Figure 9D (SEQ ID NO: 4)

GGCCCGAGTCTTGATTTTGCTCTCTCCCTGTTAAGGAGGAACATCAGGCAAGTCCAAAC
AGACCAGGGGCATTTCACCATGTTGGGTGTTAGGGATCGTTTAGCAGTCCTCCCACGTC
ACTCACAACCCGGCAAAACTATTTGGATCGAACACAAACTCGTGAACATTCTTGATGCA
GTTGAATTGGTGGATGAGCAAGGAGTCAACCTGGAATTGACCCTCATCACTCTTGACAC
TAACGAAAAGTTTAGGGATATCACCAAATTCATCCCAGAAAGTATTAGCACTGCCAGTG
ATGCCACCCTAGTGATCAACACGGAGCACATGCCCTCAATGTTTGTCCCGGTGGGTGAC
GTCGTGCAGTATGGCTTTTTGAATCTTAGTGGCAAGCCCACCCATCGCACCATGATGTA
CAACTTTCCTACTAAAGCGGGACAGTGTGGAGGAGTAGTGACATCTGTTGGGAAAGTCA
TCGGTATTCACATTGGTGGCAATGGTAGACAAGGTTTTTGCGCAGGCCTCAAAAGGAGT
TACTTTGCTAGTGAACAAGGGGAGATCCAGTGGGTTAAGCCCAATAAAGAAACTGGAAG
ACTCAACATCAATGGACCAACCCGCACCAAGTTGGAACCCAGTGTATTCCATGATGTCT
TCGAGGGAAATAAGGAACCAGCTGTCTTGCACGGCAAAGATCCCCGACTCGAGGTAGAT
TTTGAGCAGGCCCTGTTCTCTAAGTATGTGGGAAACACGCTATATGAGCCTGACGAGTA
CATCAAAGAGGCAGCTCTTCATTATGCAAATCAATTAAAGCAACTAGAAATTAATACCT
CCCAGATGAGCATGGAGGAAGCCTGCTATGGTACTGAGAATCTTGAGGCTATCGATCTT
CATACTAGTGCAGGTTACCCCTATAGTGCCCTGGGAATAAAGAAAAGAGACATCTTAGA
CCCTACCACCAGGGACGTGAGTAAAATGAAATCCTATATGGACAAATATGGTCTCGATC
TCCCTTACTCCACTTATGTCAAGGATGAGCTGCGCTCAATTGATAAAATTAAGAAAGGG
AAGTCCCGTCTGATCGAGGCCAGCAGTTTAAATGATTCAGTGTACCTCAGAATGACTTT
CGGTCATTTGTATGAGGCTTTCCACGCAAATCCTGGGACGATAACTGGATCAGCCGTGG
GGTGTAACCCTGACACATTCTGGAGCAAGCTGCCAATCTTGCTTCCTGGTTCACTCTTT
GCCTTTGACTACTCAGGTTATGATGCTAGCCTTAGCCCTGTCTGGTTCAGAGCATTAGA
AATGGTCCTTAGGGAGATAGGGTATAGTGAAGAGGCGGTCTCACTCATTGAGGGAATCA
ACCACACACACCACGTGTATCGTAACAAGACCTATTGTGTGCTTGGTGGGATGCCCTCA
GGCTGTTCGGGAACATCCATCTTCAACTCAATGATCAACAACATTATTATCAGAGCACT
GCTCATAAAAACATTTAAGGGCATTGATTTGGATGAACTCAACATGGTCGCTTATGGGG
ATGATGTGCTTGCTAGCTACCCCTTCCCAATCGATTGCTTGGAGTTAGCAAAGACTGGC
AAGGAGTATGGTCTGACCATGACTCCTGCAGATAAGTCCCCTTGCTTTAATGAAGTTAA

TO FIG. 9D (cont.)

FROM FIG. 9D

Figure 9D (cont.)

TTGGGGTAATGCGACCTTCCTCAAGAGGGGCTTTTACCTGATGAGCAGTTTCCATTTT
TGATCCACCCTACTATGCCAATGCGGGAGATCCATGAATCCATTCGATGGACTAAGGAC
GCACGAAACACTCAAGATCATGTACGGTCCTTGTGCCTCCTAGCATGGCATAATGGTAA
GCAAGAATATGAAAAATTTGTGAGCACAATTAGGTCTGTCCCAATAGGAAGAGCTTTGG
CTATCCCAAATTATGAAAATCTTAGACGCAATTGGCTCGAGTTATTT

Figure 9E (SEQ ID NO: 5)

MGSQVSTQRSGSHENSNSATEGSTINYTTINYYKDSYAATAGKQSLKQDPDKFANPVKD
IFTEMAAPLKSPSAEACGYSDRVAQLTIGNSTITTQEAANIIVGYGEWPSYCSDSDATA
VDKPTRPDVSVNRFYTLDTKLWEKSSKGWYWKFPDVLTETGVFGQNAQFHYLYRSGFCI
HVQCNASKFHQGALLVAVLPEYVIGTVAGGTGTEDSHPPYKQTQPGADGFELQHPYVLD
AGIPISQLTVCPHQWINLRTNNCATIIVPYINALPFDSALNHCNFGLLVVPISPLDYDQ
GATPVIPITITLAPMCSEFAGLRQAVTQGFPTELKPGTNQFLTTDDGVSAPILPNFHPT
PCIHIPGEVRNLLELCQVETILEVNNVPTNATSLMERLRFPVSAQAGKGELCAVFRADP
GRNGPWQSTLLGQLCGYYTQWSGSLEVTFMFTGSFMATGKMLIAYTPPGGPLPKDRATA
MLGTHVIWDFGLQSSVTLVIPWISNTHYRAHARDGVFDYYTTGLVSIWYQTNYVVPIGA
PNTAYIIALAAAQKNFTMKLCKDASDILQTGTIQGDRVADVIESSIGDSVSRALTQALP
APTGQNTQVSSHRLDTGKVPALQAAEIGASSNASDESMIETRCVLNSHSTAETTLDSFF
SRAGLVGEIDLPLEGTTNPNGYANWDIDITGYAQMRRKVELFTYMRFDAEFTFVACTPT
GEVVPQLLQYMFVPPGAPKPDSRESLAWQTATNPSVFVKLSDPPAQVSVPFMSPASAYQ
WFYDGYPTFGEHKQEKDLEYGACPNNMMGTFSVRTVGTSKSKYPLVVRIYMRMKHVRAW
IPRPMRNQNYLFKANPNYAGNSIKPTGTSRTAITTL

Figure 9F (SEQ ID NO: 6)

ATGGGTTCGCAGGTGTCCACGCAGCGCTCCGGTTCTCATGAAAATTCAAACTCAGCCAC
CGAGGGTTCCACCATAAACTACACCACCATTAATTATTACAAAGACTCCTATGCTGCCA
CAGCAGGCAAACAGAGTCTCAAGCAGGATCCAGACAAGTTTGCAAATCCTGTTAAAGAC
ATCTTCACTGAAATGGCAGCGCCACTGAAGTCCCCATCCGCTGAGGCATGTGGATACAG
TGATCGAGTAGCGCAATTAACTATTGGTAACTCCACCATCACCACGCAAGAAGCGGCTA
ACATCATAGTTGGTTATGGTGAGTGGCCTTCCTACTGCTCGGATTCTGACGCTACAGCA
GTGGATAAGCCAACGCGCCCGGATGTTTCAGTGAACAGGTTTTATACATTGGACACTAA
ATTGTGGGAGAAATCGTCCAAGGGATGGTACTGGAAATTCCCGGATGTGTTAACTGAAA
CTGGGGTTTTTGGGCAAAATGCACAATTCCACTACCTCTACCGATCAGGGTTCTGTATC
CACGTGCAGTGCAATGCTAGTAAATTCCACCAAGGAGCACTCCTAGTCGCTGTTCTACC
AGAGTACGTCATTGGGACAGTGGCAGGCGGCACAGGGACGGAAGATAGTCACCCCCCTT
ACAAGCAGACTCAACCCGGCGCCGATGGCTTCGAATTGCAACACCCGTACGTGCTTGAT
GCTGGCATCCCAATATCACAGTTAACAGTGTGCCCACATCAGTGGATTAATTTGAGAAC
CAACAATTGTGCTACAATAATAGTGCCATACATTAACGCACTGCCTTTTGATTCCGCCT
TGAACCACTGCAATTTTGGCCTATTAGTTGTGCCTATTAGCCCACTAGATTACGACCAA
GGAGCGACGCCAGTAATCCCTATAACTATCACATTAGCCCCAATGTGTTCTGAATTCGC
AGGTCTTAGGCAGGCAGTCACGCAAGGATTTCCCACCGAGTTGAAACCTGGCACAAATC
AATTTTTAACCACTGATGATGGCGTTTCAGCACCTATTCTACCAAACTTCCACCCCACC
CCGTGTATCCATATACCTGGTGAAGTTAGGAACTTGCTAGAGTTATGCCAGGTGGAAAC
CATTCTAGAGGTTAACAATGTGCCCACGAATGCCACTAGTTTAATGGAGAGACTGCGCT
TTCCAGTCTCAGCACAAGCAGGGAAAGGTGAGCTGTGTGCGGTGTTCAGAGCTGATCCT

TO FIG. 9F (cont.)

FROM FIG. 9F

Figure 9F (cont.)

GGGCGAAATGGGCCGTGGCAGTCCACCTTGCTGGGTCAGTTGTGTGGGTATTACACCCA
ATGGTCAGGATCATTGGAAGTCACCTTCATGTTTACTGGATCCTTTATGGCTACCGGCA
AGATGCTCATAGCCTATACACCGCCAGGAGGCCCTTTGCCCAAGGACCGGGCGACCGCC
ATGTTGGGCACGCACGTCATCTGGGATTTTGGGCTGCAATCGTCCGTTACCCTTGTAAT
ACCATGGATCAGCAACACTCACTACAGAGCGCATGCCCGAGATGGAGTGTTTGACTACT
ACACCACAGGGTTAGTCAGTATATGGTATCAGACAAATTACGTGGTTCCAATTGGGGCG
CCTAATACAGCCTATATAATAGCACTAGCGGCAGCCCAAAAGAATTTCACTATGAAGTT
GTGCAAGGATGCTAGTGATATCCTACAAACGGGCACCATCCAGGGAGATAGGGTAGCAG
ATGTAATTGAAAGTTCCATAGGGGATAGCGTGAGCAGAGCCCTCACTCAAGCTCTACCA
GCACCCACAGGCCAGAACACACAGGTGAGCAGTCATCGACTGGATACAGGCAAGGTTCC
AGCACTCCAAGCTGCTGAAATTGGAGCATCATCAAATGCTAGTGACGAGAGCATGATCG
AGACACGCTGTGTTCTTAACTCGCACAGCACAGCTGAGACCACTCTTGATAGTTTCTTC
AGCAGAGCGGGATTAGTTGGAGAGATAGATCTTCCTCTTGAAGGCACAACTAACCCAAA
TGGTTATGCCAACTGGGACATAGATATAACAGGTTACGCACAAATGCGCAGAAAGGTGG
AGTTATTCACCTACATGCGCTTTGATGCAGAGTTCACTTTCGTTGCGTGCACACCTACC
GGGGAAGTTGTCCCACAATTGCTCCAATATATGTTTGTACCACCTGGAGCCCCTAAGCC
AGACTCCAGGGAGTCCCTCGCATGGCAAACCGCCACCAACCCCTCAGTTTTTGTCAAGT
TGTCAGACCCTCCAGCACAGGTTTCAGTACCATTCATGTCACCCGCGAGTGCTTACCAA
TGGTTCTATGACGGATATCCCACATTCGGGGAACACAAACAGGAGAAAGATCTTGAGTA
TGGGGCGTGCCCTAATAACATGATGGGTACGTTCTCAGTGCGGACTGTAGGGACTTCCA
AATCCAAGTATCCTTTAGTGGTTAGGATTTACATGAGGATGAAGCACGTCAGGGCGTGG
ATACCTCGCCCGATGCGTAACCAAAACTACCTATTCAAGGCCAACCCAAATTATGCTGG
CAACTCCATTAAGCCAACTGGTACTAGTCGCACAGCGATCACTACTCTT

Figure 9G (SEQ ID NO: 7)

GGACCAGGGTTCGATTACGCAGTGGCTATGGCTAAAAGAAACATTGTTACAGCAACTAC
TAGCAAGGGAGAGTTCACTATGTTAGGAGTCCACGACAACGTGGCTATTTTACCAACCC
ACGCTTCACCTGGTGAAAGCATTGTGATCGATGGCAAAGAAGTGGAGATCTTGGATGCC
AAAGCGCTCGAAGATCAAGCAGGAACCAATCTTGAAATCACTATAATCACTCTAAAGAG
AAATGAAAAGTTCAGAGACATTAGACCACATATACCTACTCAAATCACTGAGACAAATG
ATGGAGTCTTGATCGTGAACACTAGCAAGTACCCCAATATGTATGTTCCTGTCGGTGCT
GTGACTGAACAGGGATATCTAAATCTCGGTGGGCGCCAAACTGCTCGTACTCTAATGTA
CAACTTTCCAACCAGAGCAGGACAGTGTGGTGGAGTCATCACATGTACTGGGAAAGTCA
TCGGGATGCATGTTGGTGGGAACGGTTCACACGGGTTTGCAGCGGCCCTGAAGCGATCA
TACTTCACTCAGAGTCAAGGTGAAATCCAGTGGATGAGACCTTCGAAGGAAGTGGGATA
TCCAATCATAAATGCCCCGTCCAAAACCAAGCTTGAACCCAGTGCTTTCCACTATGTGT
TTGAAGGGGTGAAGGAACCAGCAGTCCTCACTAAAAACGATCCCAGGCTTAAGACAGAC
TTTGAGGAGGCAATTTTCTCCAAGTACGTGGGTAACAAAATTACTGAAGTGGATGAGTA
CATGAAAGAGGCAGTAGACCACTATGCTGGCCAGCTCATGTCACTAGACATCAACACAG
AACAAATGTGCTTGGAGGATGCCATGTATGGCACTGATGGTCTAGAAGCACTTGATTTG
TCCACCAGTGCTGGCTACCCTTATGTAGCAATGGGAAAGAAGAAGAGAGACATCTTGAA
CAAACAAACCAGAGACACTAAGGAAATGCAAAAACTGCTCGACACATATGGAATCAACC
TCCCACTGGTGACTTATGTAAAGGATGAACTTAGATCCAAAACAAAGGTTGAGCAGGGG
AAATCCAGATTAATTGAAGCTTCTAGTTTGAATGACTCAGTGGCAATGAGAATGGCTTT
TGGGAACCTATATGCTGCTTTTCACAAAAACCCAGGAGTGATAACAGGTTCAGCAGTGG
GGTGCGATCCAGATTTGTTTTGGAGCAAAATTCCGGTATTGATGGAAGAGAAGCTGTTT

TO FIG. 9G (cont.)

FROM FIG. 9G

Figure 9G (cont.)

GCTTTTGACTACACAGGGTATGATGCATCTCTCAGCCCTGCTTGGTTCGAGGCACTAAA
GATGGTGCTTGAGAAAATCGGATTCGGAGACAGAGTTGACTACATCGACTACCTAAACC
ACTCACACCACCTGTACAAGAATAAAACATACTGTGTCAAGGGCGGTATGCCATCTGGC
TGCTCAGGCACTTCAATTTTTAACTCAATGATTAACAACTTGATTATCAGGACACTCTT
ACTGAAAACCTACAAGGGCATAGATTTAGACCACCTAAAAATGATTGCCTATGGTGATG
ATGTAATTGCTTCCTACCCCCATGAAGTTGACGCTAGTCTCCTAGCCCAATCAGGAAAA
GACTATGGACTAACTATGACTCCAGCTGACAAATCAGCTACATTTGAAACAGTCACATG
GGAGAATGTAACATTCTTGAAGAGATTCTTCAGGGCAGACGAGAAATACCCATTTCTTA
TTCATCCAGTAATGCCAATGAAGGAAATTCATGAATCAATTAGATGGACTAAAGATCCT
AGGAACACTCAGGATCACGTTCGCTCTCTGTGCCTTTTAGCTTGGCACAATGGCGAAGA
AGAATATAACAAATTCCTAGCTAAAATCAGGAGTGTGCCAATTGGAAGAGCTTTATTGC
TCCCAGAGTACTCAACATTGTACCGCCGTTGGCTTGACTCATTT

Figure 9H (SEQ ID NO: 8)

GPGFDYAVAMAKRNIVTATTSKGEFTMLGVHDNVAILPTHASPGESIVIDGKEVEILDA
KALEDQAGTNLEITIITLKRNEKFRDIRPHIPTQITETNDGVLIVNTSKYPNMYVPVGA
VTEQGYLNLGGRQTARTLMYNFPTRAGQCGGVITCTGKVIGMHVGGNGSHGFAAALKRS
YFTQSQGEIQWMRPSKEVGYPIINAPSKTKLEPSAFHYVFEGVKEPAVLTKNDPRLKTD
FEEAIFSKYVGNKITEVDEYMKEAVDHYAGQLMSLDINTEQMCLEDAMYGTDGLEALDL
STSAGYPYVAMGKKKRDILNKQTRDTKEMQKLLDTYGINLPLVTYVKDELRSKTKVEQG
KSRLIEASSLNDSVAMRMAFGNLYAAFHKNPGVITGSAVGCDPDLFWSKIPVLMEEKLF
AFDYTGYDASLSPAWFEALKMVLEKIGFGDRVDYIDYLNHSHHLYKNKTYCVKGGMPSG
CSGTSIFNSMINNLIIRTLLLKTYKGIDLDHLKMIAYGDDVIASYPHEVDASLLAQSGK
DYGLTMTPADKSATFETVTWENVTFLKRFFRADEKYPFLIHPVMPMKEIHESIRWTKDP
RNTQDHVRSLCLLAWHNGEEEYNKFLAKIRSVPIGRALLLPEYSTLYRRWLDSF

Figure 9I (SEQ ID NO: 9)

ATGGGTGCTCAGGTTTCATCACAGAAAGTGGGCGCACATGAAAACTCAAATAGAGCGTA
TGGTGGTTCTACCATTAATTACACCACCATTAATTATTATAGAGATTCAGCTAGTAACG
CGGCTTCGAAACAGGACTTCTCTCAAGACCCTTCCAAGTTCACCGAGCCCATCAAGGAT
GTCCTGATAAAAACAGCCCCAATGCTAAACTCGCCAAACATAGAGGCTTGCGGGTATAG
CGATAGAGTACTGCAATTAACACTGGGAAACTCCACTATAACCACACAGGAGGCGGCTA
ATTCAGTAGTCGCTTATGGGCGTTGGCCTGAATATCTGAGGGACAGCGAAGCCAATCCA
GTGGACCAGCCGACAGAACCAGACGTCGCTGCATGCAGGTTTTATACGCTAGACACCGT
GTCTTGGACGAAAGAGTCGCGAGGGTGGTGGTGGAAGTTGCCTGATGCACTGAGGGACA
TGGGACTCTTTGGGCAAAATATGTACTACCACTACCTAGGTAGGTCCGGGTACACCGTG
CATGTACAGTGTAACGCCTCCAAATTCCACCAGGGGGCACTAGGGGTATTCGCCGTACC
AGAGATGTGTCTGGCCGGGGATAGCAACACCACTACCATGCACACCAGCTATCAAAATG
CCAATCCTGGCGAGAAAGGAGGCACTTTCACGGGTACGTTCACTCCTGACAACAACCAG
ACATCACCTGCCCGCAGGTTCTGCCCGGTGGATTACCTCCTTGGAAATGGCACGTTGTT
GGGGAATGCCTTTGTGTTCCCGCACCAGATAATAAACCTACGGACCAACAACTGTGCTA
CACTGGTACTCCCTTACGTGAACTCCCTCTCGATAGATAGTATGGTAAAGCACAATAAT
TGGGGAATTGCAATATTACCATTGGCCCCATTAAATTTTGCTAGTGAGTCCTCCCCAGA
GATTCCAATCACCTTGACCATAGCCCCTATGTGCTGTGAGTTCAATGGATTAAGAAACA

TO FIG. 9I (cont.)

FROM FIG. 9I

Figure 9I (cont.)

TCACCCTGCCACGCTTACAGGGCCTGCCGGTCATGAACACCCCTGGTAGCAATCAATAT
CTTACTGCAGACAACTTCCAGTCACCGTGTGCGCTGCCTGAATTTGATGTGACCCCACC
TATTGACATACCCGGTGAAGTAAAGAACATGATGGAATTGGCAGAAATCGACACCATGA
TTCCCTTTGACTTAAGTGCCACAAAAAAGAACACCATGGAAATGTATAGGGTTCGGTTA
AGTGACAAACCACATACAGACGATCCCATACTCTGCCTGTCACTCTCTCCAGCTTCAGA
TCCTAGGTTGTCACATACTATGCTTGGAGAAATCCTAAATTACTACACACACTGGGCAG
GATCCCTGAAGTTCACGTTTCTGTTCTGTGGATTCATGATGGCAACTGGCAAACTGTTG
GTGTCATACGCGCCTCCTGGAGCCGACCCACCAAAGAAGCGTAAGGAGGCGATGTTGGG
AACACATGTGATCTGGGACATAGGACTGCAGTCCTCATGTACTATGGTAGTGCCATGGA
TTAGCAACACCACGTATCGGCAAACCATAGATGATAGTTTCACCGAAGGCGGATACATC
AGCGTCTTCTACCAAACTAGAATAGTCGTCCCTCTTTCGACACCCAGAGAGATGGACAT
CCTTGGTTTTGTGTCAGCGTGTAATGACTTCAGCGTGCGCTTGTTGCGAGATACCACAC
ATATAGAGCAAAAAGCGCTAGCACAGGGGTTAGGTCAGATGCTTGAAAGCATGATTGAC
AACACAGTCCGTGAAACGGTGGGGGCGGCAACATCTAGAGACGCTCTCCCAAACACTGA
AGCCAGTGGACCAACACACTCCAAGGAAATTCCGGCACTCACCGCAGTGGAAACTGGGG
CCACAAATCCACTAGTCCCTTCTGATACAGTGCAAACCAGACATGTTGTACAACATAGG
TCAAGGTCAGAGTCTAGCATAGAGTCTTTCTTCGCGCGGGGTGCATGCGTGACCATTAT
GACCGTGGATAACCCAGCTTCCACCACGAATAAGGATAAGCTATTTGCAGTGTGGAAGA
TCACTTATAAAGATACTGTCCAGTTACGGAGGAAATTGGAGTTCTTCACCTATTCTAGA
TTTGATATGGAACTTACCTTTGTGGTTACTGCAAATTTCACTGAGACTAACAATGGGCA
TGCCTTAAATCAAGTGTACCAAATTATGTACGTACCACCAGGCGCTCCAGTGCCCGAGA
AATGGGACGACTACACATGGCAAACCTCATCAAATCCATCAATCTTTTACACCTACGGA
ACAGCTCCAGCCCGGATCTCGGTACCGTATGTTGGTATTTCGAACGCCTATTCACACTT
TTACGACGGTTTTTCCAAAGTACCACTGAAGGACCAGTCGGCAGCACTAGGTGACTCCC
TTTATGGTGCAGCATCTCTAAATGACTTCGGTATTTTGGCTGTTAGAGTAGTCAATGAT
CACAACCCGACCAAGGTCACCTCCAAAATCAGAGTGTATCTAAAACCCAAACACATCAG
AGTCTGGTGCCCGCGTCCACCGAGGGCAGTGGCGTACTACGGCCCTGGAGTGGATTACA
AGGATGGTACGCTTACACCCCTCTCCACCAAGGATCTGACCACATAT

Figure 9J (SEQ ID NO: 10)

MGAQVSSQKVGAHENSNRAYGGSTINYTTINYYRDSASNAASKQDFSQDPSKFTEPIKD
VLIKTAPMLNSPNIEACGYSDRVLQLTLGNSTITTQEAANSVVAYGRWPEYLRDSEANP
VDQPTEPDVAACRFYTLDTVSWTKESRGWWWKLPDALRDMGLFGQNMYYHYLGRSGYTV
HVQCNASKFHQGALGVFAVPEMCLAGDSNTTTMHTSYQNANPGEKGGTFTGTFTPDNNQ
TSPARRFCPVDYLLGNGTLLGNAFVFPHQIINLRTNNCATLVLPYVNSLSIDSMVKHNN
WGIAILPLAPLNFASESSPEIPITLTIAPMCCEFNGLRNITLPRLQGLPVMNTPGSNQY
LTADNFQSPCALPEFDVTPPIDIPGEVKNMMELAEIDTMIPFDLSATKKNTMEMYRVRL
SDKPHTDDPILCLSLSPASDPRLSHTMLGEILNYYTHWAGSLKFTFLFCGFMMATGKLL
VSYAPPGADPPKKRKEAMLGTHVIWDIGLQSSCTMVVPWISNTTYRQTIDDSFTEGGYI
SVFYQTRIVVPLSTPREMDILGFVSACNDFSVRLLRDTTHIEQKALAQGLGQMLESMID
NTVRETVGAATSRDALPNTEASGPTHSKEIPALTAVETGATNPLVPSDTVQTRHVVQHR
SRSESSIESFFARGACVTIMTVDNPASTTNKDKLFAVWKITYKDTVQLRRKLEFFTYSR
FDMELTFVVTANFTETNNGHALNQVYQIMYVPPGAPVPEKWDDYTWQTSSNPSIFYTYG
TAPARISVPYVGISNAYSHFYDGFSKVPLKDQSAALGDSLYGAASLNDFGILAVRVVND
HNPTKVTSKIRVYLKPKHIRVWCPRPPRAVAYYGPGVDYKDGTLTPLSTKDLTTY

PICORNAVIRUS-LIKE PARTICLE PRODUCTION IN PLANTS

FIELD OF INVENTION

This invention relates to producing picornavirus structural proteins in plants. More specifically, the present invention also relates to producing virus-like particles comprising picornavirus structural protein in plants.

BACKGROUND OF THE INVENTION

Picornaviruses are small non-enveloped positive strand RNA viruses that can cause a wide range of clinical manifestations in humans and animals. Based on a number of properties including sequence homologies and acid sensitivity, Picornaviruses are separated into a number of genera among them are many important pathogens of humans and animals.

Picornaviruses have naked nucleocapsid. The capsid is an arrangement of 60 protomers in a tightly packed icosahedral structure. Each protomer consists of 4 polypeptides known as VP (viral protein) 1, 2, 3 and 4. VP2 and VP4 polypeptides originate from one precursor known as VP0, which is cleaved after the internalization of the viral genomic RNA into the cell. VP4 is located on the internal side of the capsid. Depending on the type and degree of dehydration the viral particle is around 27-30 nm in diameter.

Picornaviruses have a monopartite, linear, polyadenylated ssRNA(+) genome of 7.1-8.9 kb, that is composed of a single ORF encoding a polyprotein. Viral genomic RNA has a viral protein (VPg) at its 5' end instead of a methylated nucleotide cap structure. The long UTR at the 5' end contains an internal ribosome entry site (IRES). The P1 region encodes the structural polypeptides. The P2 and P3 regions encode the nonstructural proteins associated with replication. The shorter 3' UTR is important in (−)strand synthesis. L is an additional N-terminal leader protein present in some genera that can either be a protease (aphthoviruses, erboviruses) or have other function (kobuvirus, cardiovirus).

The virion RNA is infectious and serves as both the genome and viral messenger RNA. The IRES allows direct translation of the polyprotein. The polyprotein is initially processed by the viral protease(s) into various precursor and mature proteins to yield the structural proteins, replicase, VPg, and a number of proteins that modify the host cell, ultimately leading to cell lysis.

Enterovirus 71 (EV71) is a member of the Picornaviridae family of single stranded RNA viruses. It is a non-enveloped virus and its capsid is constituted of multiple coat proteins produced as fragments of a single viral translation product. The processing of viral polyprotein into structural and non-structural components is presented in FIG. 1 (prior art). The P1 region of the polyprotein gene encodes the structural proteins while P2 and P3 regions encode non-structural components of the virus. After cleavage of the structural protein precursor P1 (1ABCD in FIG. 1) from the polyprotein by the viral protease 2A, the P1 precursor is processed into the capsid proteins VP0, VP1 (1D fragment in FIG. 1) and VP3 (1C fragment in FIG. 1). The 3C component and its precursor 3CD—encoded by the P3 region—are the viral proteases responsible for processing the P1 precursor into capsid proteins. The VP0, VP1 and VP3 protomers spontaneously assemble into empty capsids and it is believed that viral RNA is packaged into the particles after the assembly of empty particles. Association of the empty capsid with genomic RNA results in a structural shift, internalization of the RNA, autocatalytic cleavage of VP0 into VP2 (1B fragment in FIG. 1) and VP4 (1A fragment in FIG. 1), and maturation into a stable 150S virion. Empty capsids, containing the uncleaved VP0 precursor, are commonly found during picornavirus infections.

Production of EV71 VLPs in insect cells has been obtained from the co-expression of the P1 precursor protein with the 3CD protease (Hu et al., 2003, Biotechnology Letters 25: 919-925). Use of a single baculovirus vector for the production of P1 and 3CD is described by Chung et al. (2008, Vaccine 26: 1855-1862) Immunogenicity studies in mice showed that purified EV71 VLPs conferred protection to a challenge with lethal doses of the virus.

The VP1 protein from EV71 has been produced in fruits of transgenic tomatoes, and feeding mice with transgenic fruit containing VP1 resulted in the development of VP1-specific fecal IgA and serum IgG (Chen et al., 2006, Vaccine 24: 2944-2951).

The P1 precursor protein and protease 3C of the foot and mouth disease virus (FMDV) was co-expressed in transgenic alfalfa (Dus Santos et al. 2005, Vaccine 23: 1838-1843). The alfalfa was stably transformed with a single vector comprising the genomic region of FMDV P1 (1A, 1B, 1C, 1D), 2A, the first 16 amino acid residues of the N terminus of 2B, the complete sequence of 3B1, 3B2, 3B3, 3C and the first 16 amino acid residues of the N terminus of 3D. Immunogenicity of crude protein extracts from the transgenic plants was demonstrated by intraperitoneal administration in Balb/c mice. Immunized mice were also protected against a lethal FMDV challenge. The levels of antigen expression were low for practical purposes.

Argentinean Application AR078257 discloses a transgenic plant expressing an empty capsid virus, wherein the transgenic plant comprises in its genome a DNA construct encoding a P1 precursor polypeptide linked to autocatalytic 2A protease. The DNA construct may further contain protein fragment 2B attached to the sequence encoding the 3C protease linked to a fragment of the sequence encoding a protein fragment 3D.

SUMMARY OF THE INVENTION

The present invention relates to producing picornavirus structural proteins in plants. More specifically, the present invention also relates to producing virus-like particles comprising picornavirus structural protein in plants.

According to the present invention there is provided a method (A) of producing a Picornavirus-like particle (PVLP) in a plant comprising:

a) introducing a first nucleic acid comprising a first regulatory region active in the plant operatively linked to a nucleotide sequence encoding one or more picornavirus polyprotein, into the plant, or portion of the plant,
b) introducing a second nucleic acid comprising a second regulatory region active in the plant and operatively linked to a second nucleotide sequence encoding one or more protease;
c) incubating the plant, portion of the plant under conditions that permit the expression of the first and second nucleic acid, thereby producing the PVLP.

The present invention also provides a method (B) of producing a Picornavirus-like particle (PVLP) comprising, a) providing a plant, portion of a plant, or plant cell comprising a first nucleic acid comprising a first regulatory region active in the plant operatively linked to a first nucleotide sequence encoding one or more picornavirus polyprotein and a second nucleic acid comprising a second regulatory region active in the plant operatively linked to a second nucleotide sequence encoding one or more protease;

b) incubating the plant, portion of the plant, or plant cell under conditions that permit the expression of the nucleic acids, thereby producing the PVLP.

The first regulatory region active in the plant, and the second regulatory region active in the plant may be the same or different.

Furthermore, in method (A) or (B) the percent ratio of the first nucleic acid to the second nucleic acid introduced into the plant, portion of the plant, or plant cell may be between 95%:5% to 50%:50%, or from between about 20:1 to about 0.5:1.

The present invention also includes the methods (A) or (B) as described above, wherein the first nucleic acid sequence comprises the first regulatory region operatively linked with a one or more than one comovirus enhancer, the nucleotide sequence encoding the polyprotein, and one or more than one geminivirus amplification element, and a third nucleic acid encoding a geminivirus replicase is introduced into the plant or portion of the plant. The one or more than one comovirus enhancer may be a comovirus UTR, for example, a Cowpea Mosaic Virus hyperanslatable (CPMV-HT) UTR such as the CPMV-HT 5', 3'UTR, or a combination thereof. The one or more than one geminivirus amplification element may be selected from a Bean Yellow Dwarf Virus long intergenic region (BeYDV LIR), and a BeYDV short intergenic region (BeYDV SIR).

The methods as described above (Method A) may also involving introducing another nucleic acid sequence encoding a suppressor of silencing, for example HcPro or p19.

The methods as described above (Method B) may also involving further providing the plant, portion of plant, or plant cell comprising another nucleic acid sequence encoding a suppressor of silencing, for example HcPro or p19.

The present invention also includes the method (A) as described above, wherein in the step of introducing (step a), the nucleic acid is transiently expressed in the plant. Alternatively, in the step of introducing (step a), the nucleic acid is stably expressed in the plant.

The methods (A) and (B) as described above may further comprising a step of harvesting the plant and purifying the PVLPs.

The present invention includes a composition comprising an effective dose of the PVLP as just described for inducing an immune response, and a pharmaceutically acceptable carrier.

The present invention also includes a method of inducing immunity to picornavirus infection in a subject, comprising administering the PVLP as just described to the subject. The PVLP may be administered to a subject orally, intradermally, intranasally, intramusclarly, intraperitoneally, intravenously, or subcutaneously.

The present invention also provides plant matter comprising a PVLP produced by the method (A) and/or (B) described above. The plant matter may be used in inducing immunity to a picornavirus infection in a subject. The plant matter may also be admixed as a food supplement.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 9A shows the 3CD from EV71 strain HK08 comprising amino acids 1549-2193 (SEQ ID NO: 1), as set forth under GenBank ID ADG57603. FIG. 9B shows 3CD from EV71 strain HK08 comprising nucleotide 5387-7321 (SEQ ID NO: 2) set forth under GenBank ID GQ279369. FIG. 9C shows 3CD from EV71 strain GDFS08 comprising amino acids 1549-2193 (SEQ ID NO: 3) as set forth under GenBank ID ACI25378. FIG. 9D shows 3CD from EV71 strain GDFS08 comprising nucleotide 5387-7321 (SEQ ID NO: 4) set forth under GenBank ID FJ194964. FIG. 9E shows P1 amino acids sequence GenBank ID ADG57603 (amino acids 1-862) (SEQ ID NO: 5). FIG. 9F shows P1 nucleotide sequence GenBank ID GQ279369 (nucleotides 743-3328) (SEQ ID NO: 6). FIG. 9G shows PVgp1 polyprotein nucleotide sequence from Human enterovirus C serotype PV-1 (GenBank ID NC_002058 for genome and NP_041277 for polyprotein: nt 5438-7369) (SEQ ID NO: 7). FIG. 9H shows amino acid sequence of polyprotein from Poliovirus (aa 1566-2209 from GenBank ID NP_041277) (SEQ ID NO: 8).

FIG. 9I shows nucleotide sequence of PVgp1 polyprotein [Human enterovirus C] (nt 743-3385 from GenBank ID NC_002058) (SEQ ID NO: 9). FIG. 9J shows amino acid sequence of polyprotein [Human enterovirus C] GenBank ID NP_041277 (aa 1-881 from GenBank ID NP_041277) (SEQ ID NO: 10).

DETAILED DESCRIPTION

Figure 1:
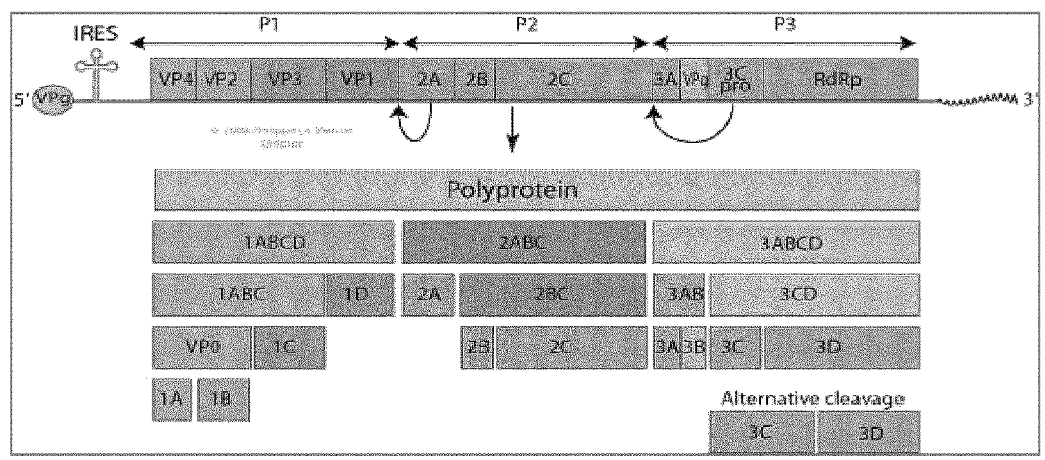
FIG. 1 shows a prior art representation of a picornavirus genome (enterovirus 71) and polyprotein processing intermediates. (from ViralZone webpage)

The following description is of a preferred embodiment.

The present invention relates to virus-like particles (VLPs) comprising one or more picornavirus structural protein (i.e. a picornavirus like protein, or PVLP), and methods of producing PVLPs in plants or in portions of the plant. The PVLP may therefore comprise one or more than one picornavirus structural protein. For example, the PVLP may comprise one or more than one enterovirus structural protein.

The picornavirus may be selected from the group of Aphthovirus, Avihepatovirus, Cardiovirus, Enterovirus, Erbovirus, Hepatovirus, Kobuvirus, Parechovirus, Sapelovirus, Senecavirus, Teschovirus and Tremovirus. In a non-limiting example the picornavirus may be an Enterovirus, for example Enterovirus 71 (EV71) or Human enterovirus C (also known as poliovirus).

The present invention in part provides a method of producing a VLP, for example a PVLP or an enterovirus like particle in a plant. The method may comprise introducing a first nucleic acid comprising a first regulatory region active in the plant operatively linked to a first nucleotide sequence encoding one or more picornavirus polyprotein into the plant, or portion of the plant and introducing a second nucleic acid comprising a second regulatory region active in the plant operatively linked to a second nucleotide sequence encoding a protease. Followed by incubating the plant or portion of the plant under conditions that permit the expression of the nucleic acids, thereby producing the PVLP.

The term "virus-like particle" (VLP), or "virus-like particles" or "VLPs" refers to structures that self-assemble and comprise one or more than one structural protein, for example one or more than one picornavirus structural protein, or one or more than one enterovirus structural protein, or a combination thereof, for example but not limited to VP0, VP1, VP2, VP3, VP4 structural protein, or a combination thereof. VLPs are generally morphologically and antigenically similar to virions produced in an infection, but lack genetic information sufficient to replicate and thus are non-infectious. VLPs may be produced in suitable host cells including plant host cells. Following extraction from the host cell and upon isolation and further purification under suitable conditions, VLPs may be purified as intact structures.

The term "Picornavirus-like particle" (PVLP), refers to a VLP or VLPs comprising one or more than one picornavirus structural protein. The term or "enterovirus-like particle" refers to a VLP or VLPs comprising one or more than one enterovirus structural protein. Example of picornavirus structural proteins may include, but not limited to VP0, VP1, VP2, VP3, VP4, or a combination thereof structural protein. Example of enterovirus structural proteins may include, but not limited to VP0, VP1, VP2, VP3, VP4, or a combination thereof, structural protein.

By polyprotein is meant a protein that comprises one or more than one protein or protein precursor, which when proteolytic processed provide one or more protein. For example the polyprotein may comprise one or more than one structural protein. The one or more proteins for example structural protein, in the polypeptide may for example be separated by cleavage sites, such for example protease cleavage sites. A non-limiting example for a "polyprotein" is the structural protein precursor P1 also referred to as "P1 region". The P1 region is defined as that part of the picornavirus polyprotein which generates "structural proteins" or "coat proteins" for example VP0, VP1, VP2, VP3, VP4 or a combination thereof. Non-limiting examples of picornavirus P1, or fragments of P1 that may be used according to the present invention include those P1 from enterovirus for example enterovirus 71.

An example of a P1 region, which is not to be considered limiting, is the amino acid sequence set forth under GenBank ID ADG57603 comprising amino acids 1-862 (SEQ ID NO: 5) or a sequence having at least about 90-100% sequence similarity thereto, including any percent similarity within these ranges, such as 90, 91, 92, 93, 94, 95, 96, 97, 98, 99, 100% sequence similarity thereto. Furthermore, a non-limiting example of a nucleotide sequence encoding a P1 region is set forth under GenBank ID GQ279369 comprising nucleotides 743-3328 (SEQ ID NO: 6) or a sequence having at least about 90-100% sequence similarity thereto, including any percent similarity within these ranges, such as 90, 91, 92, 93, 94, 95, 96, 97, 98, 99, 100% sequence similarity thereto.

Another example of a P1 region, which is not to be considered limiting, is the amino acid sequence set forth under GenBank ID NP_041277 comprising amino acids 1566-2209 (SEQ ID NO: 8) or a sequence having at least about 90-100% sequence similarity thereto, including any percent similarity within these ranges, such as 90, 91, 92, 93, 94, 95, 96, 97, 98, 99, 100% sequence similarity thereto. Furthermore, a non-limiting example of a nucleotide sequence encoding a P1 region is set forth under GenBank ID NC_002058 comprising nucleotides 5438-7369 (SEQ ID NO: 7) or a sequence having at least about 90-100% sequence similarity thereto, including any percent similarity within these ranges, such as 90, 91, 92, 93, 94, 95, 96, 97, 98, 99, 100% sequence similarity thereto. In another example which is not to be considered limiting the P1 region has the amino acid sequence set forth under GenBank ID NP_041277 comprising amino acids 1-881 (SEQ ID NO: 10) or a sequence having at least about 90-100% sequence similarity thereto, including any percent similarity within these ranges, such as 90, 91, 92, 93, 94, 95, 96, 97, 98, 99, 100% sequence similarity thereto. Furthermore, a non-limiting example of a nucleotide sequence encoding a P1 region is set forth under GenBank ID NC_002058 comprising nucleotides 743-3385 (SEQ ID NO: 9) or a sequence having at least about 90-100% sequence similarity thereto, including any percent similarity within these ranges, such as 90, 91, 92, 93, 94, 95, 96, 97, 98, 99, 100% sequence similarity thereto.

A "picornavirus polyprotein" refers to all or a portion of a picornavirus polyprotein isolated from picornavirus, present in any naturally occurring or variant picornavirus strain or isolate, for example an enterovirus polyprotein. Similarly, the "picornavirus structural protein" may refer to all or a portion of a picornavirus structural protein isolated from picornavirus, present in any naturally occurring or variant picornavirus strain or isolate, for example an enterovirus structural protein, for example obtained from a poliovirus or enterovirus 71. Thus, the term "picornavirus polyprotein" and "picornavirus structural protein" and the like include naturally occurring variants of picornavirus polyprotein, picornavirus structural protein, or a combination thereof, produced by mutation during the virus life-cycle or produced in response to selective pressure (e.g., drug therapy, expansion of host cell tropism or infectivity, etc.). The term "picornavirus polyprotein" further includes "enterovirus polyprotein" and "enterovirus structural protein" and the like include naturally occurring variants of enterovirus polyprotein, enterovirus structural protein, or a combination thereof, produced by mutation during the virus life-cycle or produced in response to selective pressure (e.g., drug therapy, expansion of host cell tropism or infectivity, etc.). The term "picornavirus polyprotein" may also include "poliovirus polyprotein" and "poliovirus structural protein" and the like include naturally occurring variants of poliovirus polyprotein, poliovirus structural protein, or a combination thereof, produced by mutation during the virus life-cycle or produced in response to selective pressure (e.g., drug therapy, expansion of host cell tropism or infectivity, etc.). As one of skill in the art appreciates, native and variants of picornavirus, enterovirus or poliovirus polyprotein, or picornavirus, enterovirus or poliovirus structural protein may be also produced using recombinant techniques.

The polyprotein may comprise one or more structural proteins for example capsid proteins. Non-limiting examples of picornavirus structural protein or capsid proteins are picornavirus protein VP0, VP1, VP2, VP3 and VP4 and a fragment of VP0, VP1, VP2, VP3 and VP4. Non-limiting examples of VP0, VP1, VP2, VP3 and VP4, or fragments of VP0, VP1, VP2, VP3 and VP4 protein that may be used according to the present invention include those VP0, VP1, VP2, VP3 and VP4 protein from enterovirus, for example poliovirus or enterovirus 71. Furthermore, the polyprotein structural protein, or a combination thereof may be for example from enterovirus 71 strain HK08 or strain GDFS08. In another non limiting example the polyprotein structural protein or a combination thereof may be from human enterovirus C, also known as poliovirus.

Amino acid sequence similarity or identity may be computed by using the BLASTP and TBLASTN programs which employ the BLAST (basic local alignment search tool) 2.0 algorithm. Techniques for computing amino acid sequence similarity or identity are well known to those skilled in the art, and the use of the BLAST algorithm is described in ALTSCHUL et al. (1990, J Mol. Biol. 215: 403-410) and ALTSCHUL et al. (1997, Nucleic Acids Res. 25: 3389-3402).

In the present invention picornavirus, enterovirus (including poliovirus) VLPs are produced in a plant, portion of a plant or plant cell, by co-expressing a nucleic acid (a first nucleic acid) encoding a picornavirus, enterovirus or poliovirus polyprotein, for example but not limited to P1, with a second nucleic acid encoding a protease, for example a picornavirus, enterovirus or poliovirus protease such as for example but not limited to 3CD, and thereby producing VLP.

An example of a protease, which is not to be considered limiting, is an amino acid sequence from the EV71 strain HK08 comprising amino acids 1549-2193, as set forth under GenBank ID ADG57603 (SEQ ID NO:1). The nucleotide sequence set forth under GenBank ID GQ279369 (SEQ ID NO:2) from nucleotide 5387 to nucleotide 7321 or a sequence having at least about 90-100% sequence similarity to SEQ ID NO:2, including any percent similarity within this range, such as 90, 91, 92, 93, 94, 95, 96, 97, 98, 99, 100% sequence similarity thereto. Another non-limiting example is the amino acid sequence from the EV71 strain GDFS08 comprising amino acids 1549-2193 as set forth under GenBank ID ACI25378 (SEQ ID NO:3). The nucleotide sequence set forth under GenBank ID FJ194964 (SEQ ID NO:4), from nucleotide 5387 to nucleotide 7321 may be used to produce the amino acid sequence. Furthermore, a sequence having between about 90-100% sequence similarity to SEQ ID NO:4, including any percent similarity within this range, such as 90, 91, 92, 93, 94, 95, 96, 97, 98, 99, 100% sequence similarity thereto.

The first nucleic acid, and second nucleic acid, may be introduced to the plant in the same step, or may be introduced to the plant sequentially.

Sequences

Non-limiting example of sequences that may be used with the present invention include:

The P1 sequence from Aphthovirus, Avihepatovirus, Cardiovirus, Enterovirus, Erbovirus, Hepatovirus, Kobuvirus, Parechovirus, Sapelovirus, Senecavirus, Teschovirus and Tremovirus may be used to produce a P1 polyprotein. In a non-limiting example sequence encoding the the P1 polyprotein may be from Enterovirus, for example Enterovirus 71 or human enterovirus C (also known as poliovirus).

Furthermore non-limiting examples of sequences that may be used to encode a protease for use as described herein include the sequence of protease 3CD, for example, obtained from Aphthovirus, Avihepatovirus, Cardiovirus, Enterovirus, Erbovirus, Hepatovirus, Kobuvirus, Parechovirus, Sapelovirus, Senecavirus, Teschovirus and Tremovirus. In a non-limiting example the sequence encoding the 3CD protease may be from Enterovirus, for example Enterovirus 71 or Poliovirus (also known as human enterovirus C).

It has been found that by introducing and co-expressing the polyprotein and the protease in the plant or portion of the plant that the yield of the VLP produced may be modulated. The polyprotein and the protease may be provided on separate nucleic acid constructs and co-expressed, or they may be provided on the same construct but each sequence differentially expressed, as required, to optimize VLP production as described below.

By "co-expressed" it is meant that two, or more than two, nucleotide sequences are expressed at about the same time within the plant, within the same tissue of the plant and within the same cells in the plant. Moreover, the two, or more than two, nucleotide sequences may need to be expressed within the same cellular compartment such as, for example, the endoplasmic reticulum, Golgi apparatus, apoplast, cytosol, mitochondria, chloroplast, peroxysome. The nucleotide sequences need not be expressed at exactly the same time. Rather, the two or more nucleotide sequences are expressed in a manner such that the encoded products have a chance to interact. For example, the protease may be expressed either before or during the period when the polyprotein is expressed so that cleavage of the polyprotein into structural proteins may take place. The two or more than two nucleotide sequences can be co-expressed using a transient expression system, where the two or more sequences are introduced within the plant at about the same time under conditions that both sequences are expressed. The two or more than two sequences may be present on different constructs, and co-expression requires introduction of each of the constructs into the plant, portion of plant or plant cell, or the two or more than two sequences may be present on one construct and the construct introduced into the plant, portion of plant or plant cell.

Alternatively, a plant comprising one of the nucleotide sequences, for example the sequence encoding the protease may be transformed, either transiently or in a stable manner, with an additional sequence encoding the polyprotein. In this case, the sequence encoding the protease may be expressed within a desired tissue, during a desired stage of development, or its expression may be induced using an inducible promoter, and the additional sequence encoding polyprotein may be expressed under similar conditions and in the same tissue, to ensure that the nucleotide sequences are co-expressed. Additionally, the sequence encoding the polyprotein may be transformed, either transiently or in a stable manner, with an additional sequence encoding the protease. In this case, the sequence encoding the polyprotein may be expressed within a desired tissue, during a desired stage of development, or its expression may be induced using an inducible promoter, and the additional sequence encoding the protease may be expressed under similar conditions and in the same tissue, to ensure that the nucleotide sequences are co-expressed.

Figure 2:
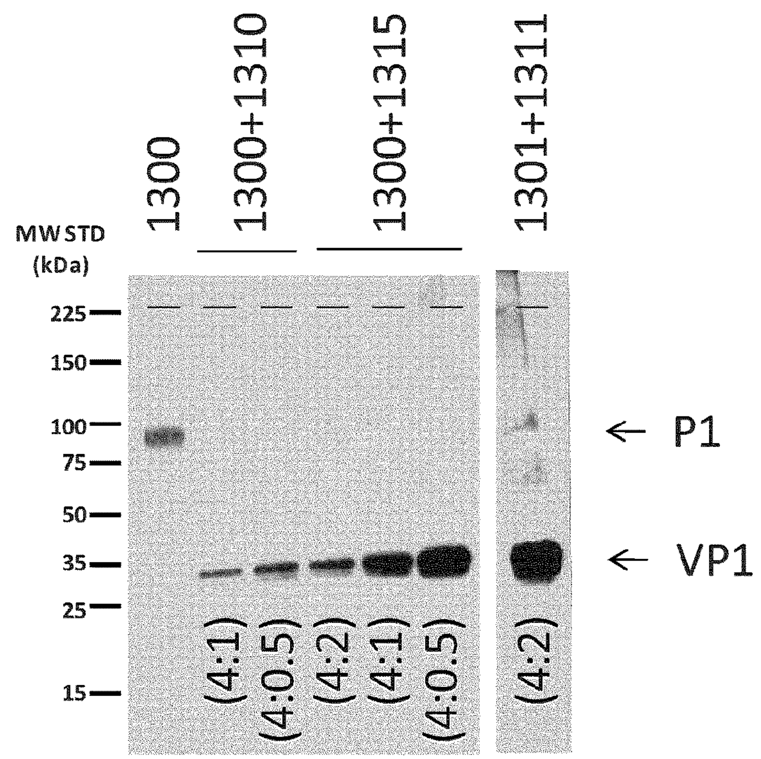
FIG. 2 shows a Western blot analysis of P1 expression and processing by 3CD. Ten micrograms of protein extracts from plants transformed with the expression vectors identified above were loaded and electrophoresed under non-reducing conditions. Mouse anti-VP1 monoclonal antibodies were used for immunodetection. The ratios indicate the proportion of P1 (construct 1300 or 1301 see table 1) to 3CD (construct 1310, 1311 or 1315 see table 1) *Agrobacterium* strains in the bacterial suspension used for transformation. The expected position of P1 and VP1 are indicated.
Figure 3:
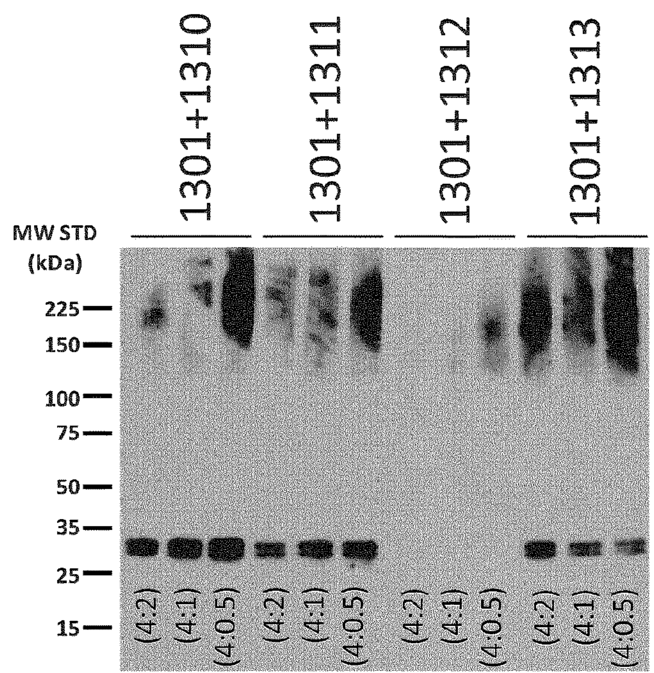
FIG. 3 shows the Screening of 3CD expression strategies for maximal accumulation of VP1. Five micrograms of protein extracts from plants transformed with the expression vectors identified above were loaded and electrophoresed under non-reducing conditions. Mouse anti-VP1 monoclonal antibodies were used for immunodetection. The ratios indicate the proportion of P1 (1301) to 3CD (1310, 1311, 1312 and 1313) *Agrobacterium* strains in the bacterial suspension used for transformation.

As may be seen in FIGS. 2 and 3, the level of VLP accumulation in the plant, portion of the plant or plant cell, is influenced by the ratio of the polyprotein-containing *Agrobacterium*, to protease-containing *Agrobacterium* infiltrated into the plant, portion of the plant or plant cell. The ratio of the polyprotein-containing to protease-containing *Agrobacterium* may range for example from about 20:1 to about 0.5:1 (polyprotein:protease), or any amount therebetween, for example from about 20:1, 18:1, 16:1, 14:1, 12:1, 10:1, 9:1, 8:1, 7:1, 6:1, 5:1, 4:1, 3:1, 2:1, 1:1, 05:1 (polyprotein:protease), or any amount therebetween.

The ratio of polyprotein to protease may be varied for example by introducing different ratios of *Agrobacterium* containing the first nucleic acid to *Agrobacterium* containing the second nucleic acid into the plant, portion of the plant or plant cell. Alternatively, if the polyprotein and protease are present on the same construct, and therefore are introduced into the same *Agrobacterium*, they may be differentially expressed within the plant, portion of the plant or plant cell using suitable promoters so that the desired ratio of polyprotein to protease is obtained.

Therefore the present invention also provides a method for increased PVLP production yield by modulating the ratio between the first and second nucleic acid.

In one embodiment the percentage of the *Agrobacterium* containing protease may be between 0.5% to 50% of total *Agrobacterium* infiltrated or any amount therebetween. For example the percent ratio of *Agrobacterium* containing protease may be 0, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49% or 50% or any amount therebetween.

The percentage ratio of *Agrobacterium* containing polyprotein to *Agrobacterium* containing protease may be 95%:5% to 40%:60% of total *Agrobacterium* infiltrated, or any amount therebetween. For example the percentage of *Agrobacterium* containing polyprotein within the total amount of *Agrobacterium* infiltrated may be 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52% or 51%. For example, the percentage ratio of *Agrobacterium* containing polyprotein to *Agrobacterium* containing protease may be between 50%:50% and 95%:5%, or any percent ratio in between, or the percentage ratio between *Agrobacterium* containing polyprotein and *Agrobacterium* containing protease may be 50%:50%, 55%:45%, 60%:40%, 65%:35%, 70%:30%, 75%:25%, 80%:20%, 85%:15%, 90%:10%, 95%:5%, or any percentage ratio in between.

Expression of the first and second nucleotide sequence within a plant cell forms a VLP, and the VLP may be used for example to produce an antibody that is capable of binding a virus protein such for example picornavirus structural protein, including but not limited to VP0, VP1, VP2, VP3 and/or VP4. The VLP, when administered to a subject, induces an immune response.

As described further below the ratio of polyprotein to protease may further be varied for example by differentially expressing the polyprotein and the protease. Expression may be varied by modulating for example replication, transcription, translation, or a combination thereof, of the polyprotein, the protease, or both the protein and the protease. For example different regulatory elements, including promoters, amplification elements, enhancers or a combination thereof, may be used in addition to varying the ratio of the polyprotein-containing *Agrobacterium* to protease-containing *Agrobacterium* infiltrated as described above. A first set or combination of regulatory elements may be used to regulate the replication, transcription or a combination thereof, of the first nucleic acid and a second set or combination of regulatory elements may be used to regulate the replication, transcription or a combination thereof, of the second nucleic acid. The first set or combination of regulatory elements is different from the second set or combination of regulatory elements and permits differential expression of the first and second nucleic acids to permit modulating the ratio of polyprotein:protease in vivo. For example, which is not to be considered limiting, one set or combination of regulatory elements, for example the first set, may include an amplification element for example elements obtained from BeYDV, while the amplification element, for example those obtained from BeYDV, may be absent in the other set or combination of regulatory elements, for example the second set. Alternatively, the second ser may include an amplification element (for example elements obtained from BeYDV), while the amplification element (for example elements obtained from BeYDV) may be absent in the first set or combination of regulatory elements. In a similar manner, the strength of a promoters may differ between the first and second set or combination of regulatory elements, or one of the promoters may be inducible, and the other constitutive, so that differential expression between the polyprotein relative to the protease is achieved in vivo.

Size

The occurrence of VLPs may be detected using any suitable method for example, sucrose gradients, or size exclusion chromatography. VLPs may be assessed for structure and size by, for example electron microscopy, or by size exclusion chromatography.

For size exclusion chromatography, total soluble proteins may be extracted from plant tissue by homogenizing (Polytron) sample of frozen-crushed plant material in extraction buffer, and insoluble material removed by centrifugation. Concentration by PEG-assisted precipitation may also be of benefit. The VLP may also be produced by preparing protoplasts or a protoplast fraction using the methods described in WO 2011/035422 (which is incorporated herein by reference). The soluble protein is quantified, and the extract passed through a Sephacryl™ column, for example a Sephacryl™ S500 column. Blue Dextran 2000 may be used as a calibration standard.

Cellular debris might be eliminated by centrifugation. The centrifuged extract may then be filtered. Without wishing to be bound by theory it is believed that such filter step or steps may remove solids in suspension, reduce bioburden and stabilize and condition the extract prior to further purification. Due to their size, PVLP may be further purified using tangential flow filtration (TFF). Without wishing to be bound by theory, TFF efficiently and selectively eliminates soluble proteins of lower molecular weight found in the clarified extract, including enzymes used for cell wall depolymerisation. Furthermore, the TFF step also concentrates VLPs and enables a buffer exchange in preparation for chromatography. The TFF step might be followed by several chromatographic steps, for example anion exchange, cation exchange, hydrophobic interaction chromatography (HIC) and/or pseudo-affinity. Additional TFF steps may be added following the chromatograph steps. Following chromatography and/or TFF, fractions may be further analyzed by immunoblot to determine the protein complement of the fraction.

The separated fraction may be for example a supernatant (if centrifuged, sedimented, or precipitated), or a filtrate (if filtered), and is enriched for proteins, or suprastructure proteins, such as for example higher-order, higher molecular weight, particles, or complete VLPs. The separated fraction may be further processed to isolate, purify, concentrate or a combination thereof, the proteins, suprastructure proteins or higher-order particles by, for example, additional centrifugation steps, precipitation, chromatographic steps (e.g. size exclusion, ion exchange, affinity chromatography), tangential flow filtration, or a combination thereof. The presence of purified proteins, suprastructure proteins or higher-order particles such as VLPs, may be confirmed by, for example, native or SDS-PAGE, Western analysis using an appropriate detection antibody, capillary electrophoresis, electron microscopy, or any other method as would be evident to one of skill in the art.

Figure 4:
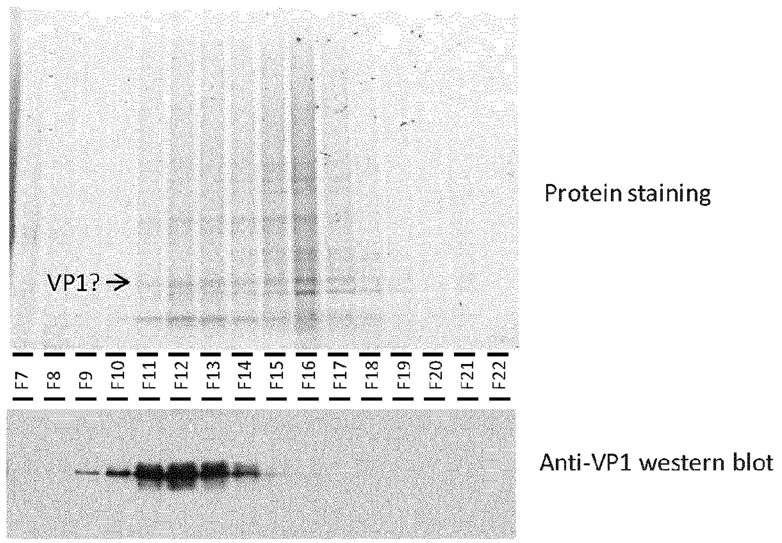
FIG. 4 shows the assessment of EV71 capsid assembly. (A) Coomassie-stained SDS-PAGE and western blot analysis of elution fractions from size exclusion chromatography (SEC) separation of protein extracts from plants co-expressing P1 and 3CD (constructs 1301+1310 (4:0.5)). The band putatively corresponding to VP1 in the Coomassie-stained gel is indicated. (B) Negative staining transmission electron microscopy examination of SEC elution fraction 12. The bar represents 100 nm.
Figure 4:
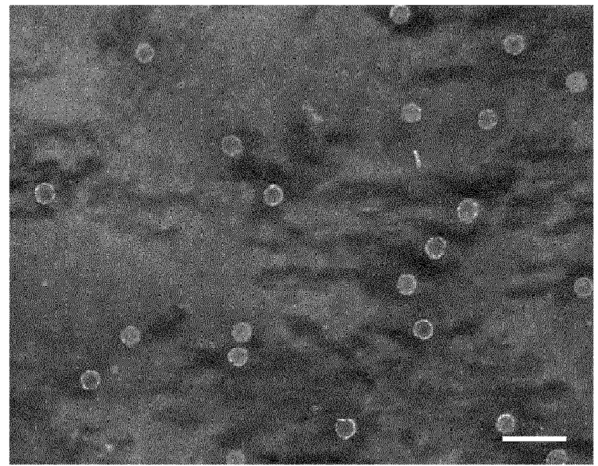

FIG. 4A, show an example of an elution profile of a size exclusion chromatography analysis of a plant extract comprising PVLPs. In this case, VLPs comprising enterovirus EV71 capsid, elute in fractions 9 to approx. 14, peaking in fraction 12.

The VLPs may be purified or extracted using any suitable method for example chemical or biochemical extraction. VLPs can be relatively sensitive to desiccation, heat, pH, surfactants and detergents. Therefore it may be useful to use methods that maximize yields, minimize contamination of the VLP fraction with cellular proteins, maintain the integrity of the proteins, or VLPs, and, methods of loosening the cell wall to release the proteins, or VLP. For example, methods that produce protoplasts and/or spheroplasts may be used (see for example WO 2011/035422, which is incorporated herein by reference) to obtain VLPs as described herein. Minimizing or eliminating the use of detergents or surfactants such for example SDS or Triton X-100 may be beneficial for improving the yield of VLP extraction. VLPs may be then assessed for structure and size by, for example, electron microscopy, or by size exclusion chromatography as mentioned above, and submitted to analytical ultracentrifugation.

The size (i.e. the diameter) of the above-defined PVLPs, maybe measured for example by dynamic light scattering (DLS) or electron microscope (EM) techniques, is usually between 20 to 50 nm, or any size therebetween. For example, the size of the intact PVLP structure may range from about 25 nm to about 35 nm, or any size therebetween, or from 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, 50 nm, or any size therebetween.

PVLP may be synthesized at an amount of up to 2 g per kilogram of plant fresh weight, corresponding to about 40% of the total protein content of the plant. For example, as described herein the amount of synthesized VLP maybe between 10 mg and 2.0 g per kilogram of fresh weight, or any amount there between, such as 10, 20, 30, 40, 50, 60, 70, 80, 90, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1600, 1700, 1800, 1900 or 2000 mg per kilogram of fresh weight or any amount therebetween.

Host

The one or more than one genetic constructs of the present invention may be expressed in any suitable plant host or portion of the plant, for example, one or more leaves, the stem plus one or more leaves, or the roots, that is transformed by the nucleotide sequence, or constructs, or vectors of the present invention. Examples of suitable hosts include, but are not limited to, agricultural crops including alfalfa, canola, *Brassica* spp., maize, *Nicotiana* spp., potato, ginseng, pea, oat, rice, soybean, wheat, barley, sunflower, cotton and the like.

The one or more genetic constructs of the present invention can further comprise a 3' untranslated region. A 3' untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon. Non-limiting examples of suitable 3' regions are the 3' transcribed non-translated regions containing a polyadenylation signal of *Agrobacterium* tumor inducing (Ti) plasmid genes, such as the nopaline synthase (NOS) gene, plant genes such as the soybean storage protein genes, the small subunit of the ribulose-I, 5-bisphosphate carboxylase gene (ssRUBISCO; U.S. Pat. No. 4,962,028; which is incorporated herein by reference), the promoter used in regulating plastocyanin expression, described in U.S. Pat. No. 7,125,978 (which is incorporated herein by reference).

One or more of the genetic constructs of the present invention may also include further enhancers, either translation or transcription enhancers, as may be required. Enhancers may be located 5' or 3' to the sequence being transcribed. Enhancer regions are well known to persons skilled in the art, and may include an ATG initiation codon, adjacent sequences or the like. The initiation codon, if present, may be in phase with the reading frame ("in frame") of the coding sequence to provide for correct translation of the transcribed sequence.

The constructs of the present invention can be introduced into plant cells using Ti plasmids, Ri plasmids, plant virus vectors, direct DNA transformation, micro-injection, electroporation, etc. For reviews of such techniques see for example Weissbach and Weissbach, *Methods for Plant Molecular Biology*, Academy Press, New York VIII, pp. 421-463 (1988); Geierson and Corey, *Plant Molecular Biology,* 2d Ed. (1988); and Miki and Iyer, *Fundamentals of Gene Transfer in Plants*. In *Plant Metabolism,* 2d Ed. D T. Dennis, D H Turpin, D D Lefebrve, D B Layzell (eds), Addison Wesly, Langmans Ltd. London, pp. 561-579 (1997). Other methods include direct DNA uptake, the use of liposomes, electroporation, for example using protoplasts, micro-injection, microprojectiles or whiskers, and vacuum infiltration. See, for example, Bilang, et al. (Gene 100: 247-250 (1991), Scheid et al. (Mol. Gen. Genet. 228: 104-112, 1991), Guerchc et al. (Plant Science 52: 111-116, 1987), Neuhause et al. (Theor. Appl Genet. 75: 30-36, 1987), Klein et al., Nature 327: 70-73 (1987); Howell et al. (Science 208: 1265, 1980), Horsch et al. (Science 227: 1229-1231, 1985), DeBlock et al., Plant Physiology 91: 694-701, 1989), Methods for Plant Molecular Biology (Weissbach and Weissbach, eds., Academic Press Inc., 1988), Methods in Plant Molecular Biology (Schuler and Zielinski, eds., Academic Press Inc., 1989), Liu and Lomonossoff (J Virol Meth, 105:343-348, 2002), U.S. Pat. Nos. 4,945,050; 5,036,006; and 5,100,792, U.S. patent application Ser. No. 08/438,666, filed May 10, 1995, and Ser. No. 07/951,715, filed Sep. 25, 1992, (all of which are hereby incorporated by reference).

Transient Expression

Without wishing to be bound by theory, the protein concentration and ratio of the different picornavirus structural proteins, the picornavirus polyprotein and/or the protease may be important for the assembly efficiency of PVLPs. Therefore multiplicity and time of infection, may be important to manipulate protein concentration and the overall assembly efficiency of VLPs in plants.

The construct of the present invention may be transiently expressed in a plant, portion of a plant, or a plant cell. A transient expression system relying on the epichromosomal expression of recombinant polyprotein introduced, via *Agrobacterium tumefaciens* infiltration, into a plant, portion of a plant, or a plant cell may be used to express the picornavirus structural protein, picornavirus polyprotein and/or protease, targeted to various cell compartments or sub-compartments. A transient expression system allows for a high production speed. Furthermore, large amounts of protein can be attained within a few days after infiltration of recombinant *Agrobacterium* in plants (Rybicki, 2010; Fischer et al., 1999). It is also possible to express long gene sequences and have more than one gene simultaneously expressed in the same cell, allowing for efficient assembly of multimeric proteins (Lombardi et al., 2009).

However, during transient expression post-transcriptional gene silencing may limit the expression of the heterologous proteins in plants. The co-expression of a suppressor of silencing, for example, but not limited to Nss from Tomato spotted wilt virus may be used to counteract the specific degradation of transgene mRNAs (Brigneti et al., 1998). Alternate suppressors of silencing are well known in the art and may be used as described herein (Chiba et al., 2006, Virology 346:7-14; which is incorporated herein by reference), for example but not limited to HcPro, TEV-p1/HC-Pro (Tobacco etch virus-p1/HC-Pro), BYV-p21, p19 of Tomato bushy stunt virus (TBSV p19), capsid protein of Tomato crinkle virus (TCV-CP), 2b of Cucumber mosaic virus; CMV-2b), p25 of Potato virus X (PVX-p25), p11 of Potato virus M (PVM-p11), p11 of Potato virus S (PVS-p11), p16 of Blueberry scorch virus, (BScV-p16), p23 of Citrus tristexa virus (CTV-p23), p24 of Grapevine leafroll-associated virus-2, (GLRaV-2 p24), p10 of Grapevine virus A, (GVA-p10), p14 of Grapevine virus B (GVB-p14), p10 of Heracleum latent virus (HLV-p10), or p16 of Garlic common latent virus (GCLV-p16). Therefore, a suppressor of silencing, for example HcPro, TEV-p1/HC-Pro, BYV-p21, TBSV p19, TCV-CP, CMV-2b, PVX-p25, PVM-p11, PVS-p11, BScV-p16, CTV-p23, GLRaV-2 p24, GBV-p14, HLV-p10, GCLV-p16 or GVA-p10, may be co-expressed along with one or more picornavirus structural protein, picornavirus polyprotein and/or protease to further ensure high levels of protein production within a plant, portion of a plant or plant cell.

The present invention also provides a method as described above, wherein an additional (third) nucleotide sequence is expressed within the plant, the additional (third) nucleotide sequence encoding a suppressor of silencing is operatively linked with an additional (third) regulatory region that is active in the plant. The nucleotide sequence encoding a suppressor of silencing may be, for example Nss, HcPro, TEV-p1/HC-Pro, BYV-p21, TBSV p19, TCV-CP, CMV-2b, PVX-p25, PVM-p11, PVS-p11, BScV-p16, CTV-p23, GLRaV-2 p24, GBV-p14, HLV-p10, GCLV-p16 or GVA-p10.

As described below, transient expression methods may be used to express the constructs of the present invention (see Liu and Lomonossoff, 2002, Journal of Virological Methods, 105:343-348; which is incorporated herein by reference). Alternatively, a vacuum-based transient expression method, as described by Kapila et al., 1997, which is incorporated herein by reference) may be used. These methods may include, for example, but are not limited to a method of Agro-inoculation or Agro-infiltration, syringe infiltration, however, other transient methods may also be used as noted above. With Agro-inoculation, Agro-infiltration, or syringe infiltration, a mixture of Agrobacteria comprising the desired nucleic acid enter the intercellular spaces of a tissue, for example the leaves, aerial portion of the plant (including stem, leaves and flower), other portion of the plant (stem, root, flower), or the whole plant. After crossing the epidermis the Agrobacteria infect and transfer t-DNA copies into the cells. The t-DNA is episomally transcribed and the mRNA translated, leading to the production of the protein of interest in infected cells, however, the passage of t-DNA inside the nucleus is transient.

Also considered part of this invention are transgenic plants, plant cells or seeds containing the nucleic acids or one or more than one gene construct of the present invention. Methods of regenerating whole plants from plant cells are also known in the art. In general, transformed plant cells are cultured in an appropriate medium, which may contain selective agents such as antibiotics, where selectable markers are used to facilitate identification of stably transformed plant cells. To aid in identification of stably transformed plant cells, the constructs of this invention may be further manipulated to include plant selectable markers. Useful selectable markers include enzymes that provide for resistance to chemicals such as an antibiotic for example, gentamycin, hygromycin, kanamycin, or herbicides such as phosphinothrycin, glyphosate, chlorosulfuron, and the like. Similarly, enzymes providing for production of a compound identifiable by colour change such as GUS (beta-glucuronidase), or luminescence, such as luciferase or GFP, may be used. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques. Transgenic plants can also be generated without using tissue cultures.

Amplification Elements

The ratio of polyprotein to protease may be varied for example by using different regulatory elements, or combination of regulatory elements, in the nucleic acid sequences used to drive expression of the polyprotein and protease. For example, a first set or combination of regulatory elements may be used to regulate the replication, transcription or a combination thereof, of the first nucleic acid and a second set or combination of regulatory elements may be used to regulate the replication, transcription or a combination thereof, of the second nucleic acid so that a difference in the expression of the first and second nucleic acids is achieved thereby modulating the ratio of polyprotein:protease in vivo. For example, which is not to be considered limiting the first set or combination of regulatory elements may include an amplification element, for example, elements obtained from BeYDV, while the amplification element may be absent in the second set or combination of regulatory elements. Alternatively, the second set may include an amplification element, for example, elements obtained from BeYDV, while the amplification element may be absent in the first set or combination of regulatory elements.

"Expression cassette" refers to a nucleotide sequence comprising a nucleic acid of interest under the control of, and operably (or operatively) linked to, an appropriate promoter or other regulatory elements for transcription of the nucleic acid of interest in a host cell.

The expression system as described herein may comprise an expression cassette based on a bipartite virus, or a virus with a bipartite genome. For example, the bipartite viruses may be of the Comoviridae family. Genera of the Comoviridae family include *Comovirus, Nepovirus, Fabavirus, Cheravirus* and *Sadwavirus*. Comoviruses include Cowpea mosaic virus (CPMV), Cowpea severe mosaic virus (CPSMV), Squash mosaic virus (SqMV), Red clover mottle virus (RCMV), Bean pod mottle virus (BPMV), Turnip ringspot virus (TuRSV), Broad bean true mosaic virus (BBtMV), Broad bean stain virus (BBSV), Radish mosaic virus (RaMV). Examples of comoviruse RNA-2 sequences comprising enhancer elements that may be useful for various aspects of the invention include, but are not limited to: CPMV RNA-2 (GenBank Accession No. NC_003550), RCMV RNA-2 (GenBank Accession No. NC_003738), BPMV RNA-2 (GenBank Accession No. NC_003495), CPSMV RNA-2 (GenBank Accession No. NC_003544), SqMV RNA-2 (GenBank Accession No. NC_003800), TuRSV RNA-2 (GenBank Accession No. NC_013219.1). BBtMV RNA-2 (GenBank Accession No. GU810904), BBSV RNA2 (GenBank Accession No. FJ028650), RaMV (GenBank Accession No. NC_003800)

Segments of the bipartite comoviral RNA genome are referred to as RNA-1 and RNA-2. RNA-1 encodes the proteins involved in replication while RNA-2 encodes the proteins necessary for cell-to-cell movement and the two capsid proteins. Any suitable comovirus-based cassette may be used including CPMV, CPSMV, SqMV, RCMV, or BPMV, for example, the expression cassette may be based on CPMV.

The expression systems may also comprise amplification elements from a geminivirus for example, an amplification element from the bean yellow dwarf virus (BeYDV). BeYDV belongs to the Mastreviruses genus adapted to dicotyledonous plants. BeYDV is monopartite having a single-strand circular DNA genome and can replicate to very high copy numbers by a rolling circle mechanism. BeYDV-derived DNA replicon vector systems have been used for rapid high-yield protein production in plants.

As used herein, the phrase "amplification elements" refers to a nucleic acid segment comprising at least a portion of one ore more long intergenic regions (LIR) of a geminivirus genome. As used herein, "long intergenic region" refers to a region of a long intergenic region that contains a rep binding site capable of mediating excision and replication by a geminivirus Rep protein. In some aspects, the nucleic acid segment comprising one or more LIRs, may further comprises a short intergenic region (SIR) of a geminivirus genome. As used herein, "short intergenic region" refers to the complementary strand (the short IR (SIR) of a Mastreviruses). Any suitable geminivirus-derived amplification element may be used herein. See, for example, WO2000/20557; WO2010/025285; Zhang X. et al. (2005, *Biotechnology and Bioengineering*, Vol. 93, 271-279), Huang Z. et al. (2009, *Biotechnology and Bioengineering*, Vol. 103, 706-714), Huang Z. et al. (2009, *Biotechnology and Bioengineering*, Vol. 106, 9-17); which are herein incorporated by reference).

Regulatory Element

The present invention is further directed to a gene construct comprising a nucleic acid encoding a polyprotein, such as one or more picornavirus protein, or a protease, for example but not limited to picornavirus protease, as described above, operatively linked to a regulatory element that is operative in a plant.

The use of the terms "regulatory region", "regulatory element" or "promoter" in the present application is meant to reflect a portion of nucleic acid typically, but not always, upstream of the protein coding region of a gene, which may be comprised of either DNA or RNA, or both DNA and RNA. When a regulatory region is active, and in operative association, or operatively linked, with a gene of interest, this may result in expression of the gene of interest. A regulatory element may be capable of mediating organ specificity, or controlling developmental or temporal gene activation. A "regulatory region" may includes promoter elements, core promoter elements exhibiting a basal promoter activity, elements that are inducible in response to an external stimulus, elements that mediate promoter activity such as negative regulatory elements or transcriptional enhancers. "Regulatory region", as used herein, may also includes elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region.

Examples of regulatory elements operative in a plant cell and that may be used in accordance with the present invention include but are not limited to a plastocyanin regulatory region (U.S. Pat. No. 7,125,978; which is incorporated herein by reference), or a regulatory region of Ribulose 1,5-bisphosphate carboxylase/oxygenase (RuBisCO; U.S. Pat. No. 4,962,028; which is incorporated herein by reference), chlorophyll a/b binding protein (CAB; Leutwiler et al; 1986; which is incorporated herein by reference), ST-LS1 (associated with the oxygen-evolving complex of photosystem II and described by Stockhaus et al. 1987, 1989; which is incorporated herein by reference).

In the context of this disclosure, the term "regulatory element" or "regulatory region" typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory element that provides for the recognition for RNA polymerase or other transcriptional factors to ensure initiation at a particular site is a promoter element. Most, but not all, eukaryotic promoter elements contain a TATA box, a conserved nucleic acid sequence comprised of adenosine and thymidine nucleotide base pairs usually situated approximately 25 base pairs upstream of a transcriptional start site. A promoter element comprises a basal promoter element, responsible for the initiation of transcription, as well as other regulatory elements (as listed above) that modify gene expression.

There are several types of regulatory regions, including those that are developmentally regulated, inducible or constitutive. A regulatory region that is developmentally regulated, or controls the differential expression of a gene under its control, is activated within certain organs or tissues of an organ at specific times during the development of that organ or tissue. However, some regulatory regions that are developmentally regulated may preferentially be active within certain organs or tissues at specific developmental stages, they may also be active in a developmentally regulated manner, or at a basal level in other organs or tissues within the plant as well. Examples of tissue-specific regulatory regions, for example see-specific a regulatory region, include the napin promoter, and the cruciferin promoter (Rask et al., 1998, J. Plant Physiol. 152: 595-599; Bilodeau et al., 1994, Plant Cell 14: 125-130). An example of a leaf-specific promoter includes the plastocyanin promoter (see U.S. Pat. No. 7,125,978, which is incorporated herein by reference).

An inducible regulatory region is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory region to activate transcription may be present in an inactive form, which is then directly or indirectly converted to the active form by the inducer. However, the protein factor may also be absent. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory region may be exposed to an inducer by externally applying the inducer to the cell or plant such as by spraying, watering, heating or similar methods. Inducible regulatory elements may be derived from either plant or non-plant genes (e.g. Gatz, C. and Lenk, L R. P., 1998, Trends Plant Sci. 3, 352-358; which is incorporated by reference). Examples, of potential inducible promoters include, but not limited to, tetracycline-inducible promoter (Gatz, C., 1997, Ann Rev. Plant Physiol. Plant Mol. BioI. 48, 89-108; which is incorporated by reference), steroid inducible promoter (Aoyama. T. and Chua, N. H., 1997, Plant 1. 2, 397-404; which is incorporated by reference) and ethanol-inducible promoter (Salter, M. G., et al, 1998, Plant 10urnal 16, 127-132; Caddick, M. X., et al, 1998, Nature Biotech. 16, 177-180, which are incorporated by reference) cytokinin inducible IB6 and CKI 1 genes (Brandstatter, I. and K.ieber, 1.1., 1998, Plant Cell 10, 1009-1019; Kakimoto, T., 1996, Science 274, 982-985; which are incorporated by reference) and the auxin inducible element, DR5 (Ulmasov, T., et aI., 1997, Plant Cell 9, 1963-1971; which is incorporated by reference).

A constitutive regulatory region directs the expression of a gene throughout the various parts of a plant and continuously throughout plant development. Examples of known constitutive regulatory elements include promoters associated with the CaMV 35S transcript (Odell et aI., 1985, Nature, 313: 810-812), the rice actin 1 (Zhang et aI, 1991, Plant Cell, 3: 1155-1165), actin 2 (An et al., 1996, *Plant J.,* 10: 107-121), or tms 2 (U.S. Pat. No. 5,428,147, which is incorporated herein by reference), and triosephosphate isomerase 1 (Xu et. al., 1994, Plant Physiol. 106: 459-467) genes, the maize ubiquitin 1 gene (Cornejo et ai, 1993, Plant Mol. BioI. 29: 637-646), the *Arabidopsis* ubiquitin 1 and 6 genes (Holtorf et aI, 1995, Plant Mol. BioI. 29: 637-646), and the tobacco translational initiation factor 4A gene (Mandel et aI, 1995, Plant Mol. BioI. 29: 995-1004).

The term "constitutive" as used herein does not necessarily indicate that a gene under control of the constitutive regulatory region is expressed at the same level in all cell types, but that the gene is expressed in a wide range of cell types even though variation in abundance is often observed. Constitutive regulatory elements may be coupled with other sequences to further enhance the transcription and/or translation of the nucleotide sequence to which they are operatively linked. For example, the CPMV-HT system is derived from the untranslated regions of the Cowpea mosaic virus (CPMV) and demonstrates enhanced translation of the associated coding sequence. By "native" it is meant that the nucleic acid or amino acid sequence is naturally occurring, or "wild type". By "operatively linked" it is meant that the particular sequences, for example a regulatory element and a coding region of interest, interact either directly or indirectly to carry out an intended function, such as mediation or modulation of gene expression. The interaction of operatively linked sequences may, for example, be mediated by proteins that interact with the operatively linked sequences.

The ratio of polyprotein to protease may further be varied for example by using regulatory elements, amplification element and/or enhancers. For example the first nucleic acid may comprise a regulatory elements, amplification element and/or enhancers. The second nucleic acid may or may not comprise the same combination of a regulatory elements, amplification element and/or enhancers.

For example, different promoters may be used to drive differential expression between the polyprotein relative to the protease in vivo. For example, the first set or combination of regulatory elements may include an inducible promoter, while the promoter in the second set or combination of regulatory elements may be constitutive, or the second set or combination of regulatory elements may comprise an inducible promoter, while the promoter in the first set or combination of regulatory elements may be constitutive. The strength of the promoter may also differ between the first and second set or combination of regulatory elements, so that differential expression between the polyprotein relative to the protease is achieved in vivo.

The present invention will be further illustrated in the following examples.

Example 1 Expression EV71

Gene Synthesis

DNA segments encoding EV71 structural protein P1 and protease 3CD were used. The candidate sequences for P1 and 3CD are available in GenBank. Non limiting examples of these sequences are:

- For P1aa sequence: amino acids sequence GenBank ID ADG57603 (amino acids 1-862) (SEQ ID NO:5); nucleotide sequence: GenBank ID GQ279369 (nucleotides 743-3328) (SEQ ID NO:6);
- For 3CD (strain HK08): amino acid sequence: GenBank ID ADG57603 (amino acids 1549-2193) (SEQ ID NO:

1); nucleotide sequence: GenBank ID GQ279369 (nucleotides 5386-7321) (SEQ ID NO:2);

For 3CD (strain GDFS08): amino acid sequence GenBank ID ACI25378 (amino acids 1549-2193)(SEQ ID NO: 3); nucleotide sequence: GenBank ID FJ194964 (nucleotides 5387-7321) (SEQ ID NO: 4).

Two P1 genes were synthesized. The first was produced using the wild-type sequence while the second was based on an optimized sequence (human codon usage) determined using standard methods as known in the art. The two 3CD genes were synthesized based on their wild-type sequences. The 3 wild-type genes were synthesized by Invitrogen™ (formerly GeneArt®) and the optimized P1 gene was optimized and synthesized by DNA2.0.

Molecular Cloning

The synthesized genes were cloned into plant expression vectors. Selected vector components include transcription and translation regulatory elements from a cowpea mosaic virus (CPMV)-based cassette or an alfalfa plastocyanin gene. Both regulatory elements have been used with success in our platform for high expression of recombinant proteins. DNA amplification elements from the Bean yellow dwarf geminivirus (BeYDV) are another feature that can be integrated into our plant expression vectors. It has led to a great increase in protein expression for some candidates. We have therefore cloned each gene construct in expression vectors with or without DNA amplification elements. Table 1 presents the plant expression cassettes assembled for the project.

TABLE 1

Plant expression cassettes assembled for the expression of EV71 structural polyprotein P1 and protease 3CD in *N. benthamiana.*

| Coding region | Regulatory element | DNA amplification elements | Vector number |
|---|---|---|---|
| P1 (Wt HK08) | CPMV HT | — | 1300 |
| P1 (Wt HK08) | CPMV HT | BeYDV + rep | 1301 |
| P1 (Wt HK08) | Plastocyanin | — | 1302 |
| P1 (Wt HK08) | Plastocyanin | BeYDV + rep | 1303 |
| P1 (Opt HK08) | CPMV HT | — | 1305 |
| P1 (Opt HK08) | CPMV HT | BeYDV + rep | 1306 |
| P1 (Opt HK08) | Plastocyanin | — | 1307 |
| P1 (Opt HK08) | Plastocyanin | BeYDV + rep | 1308 |
| 3CD (Wt HK08) | CPMV HT | — | 1310 |
| 3CD (Wt HK08) | CPMV HT | BeYDV + rep | 1311 |
| 3CD (Wt HK08) | Plastocyanin | — | 1312 |
| 3CD (Wt HK08) | Plastocyanin | BeYDV + rep | 1313 |
| 3CD (Wt GDFS08) | CPMV HT | — | 1315 |
| 3CD (Wt GDFS08) | CPMV HT | BeYDV + rep | 1316 |
| 3CD (Wt GDFS08) | Plastocyanin | — | 1317 |
| 3CD (Wt GDFS08) | Plastocyanin | BeYDV + rep | 1318 |

Analysis of Expression—Selecting the Best Recombinant Gene Constructs

Each expression cassettes was cloned into a plasmid vector that was then transferred to *Agrobacterium tumefaciens*. Transient expression was initiated by vacuum infiltration of the transgenic *Agrobacterium* inoculum that leads to transfer of mobile DNA copies of the DNA constructs into plant cells. Transient expression of multiple components (co-expression) was performed by infiltration of mixes of *Agrobacterium* inoculums (co-infiltration). As one component being introduced into the plant was structural (P1), and the substrate of the second component, the 3CD protease, the level of expression of the two components was modulated. This was performed by the use of different promoters, DNA amplification systems of variable strength, by varying the relative abundance of each inoculum (P1 and 3CD) at the time of infiltration, or a combination thereof.

Expression vectors 1300 to 1308 were screened for their ability to express P1 alone, and when combined with vectors 1310 to 1318, for their ability to produce high levels of the proteolytic fragments VP1-4. As only an anti-VP1 antibody was available (Abnova, MAB1255-M05), accumulation of proteolytic fragments was monitored through accumulation of VP1 and disappearance of unprocessed P1. As shown in FIG. 2, the expression of P1 alone (vector no. 1300) led to the accumulation of a VP1-containing product having an apparent molecular weight corresponding to that of the unprocessed structural protein (98 kDa), indicating that plant proteases cannot cleave P1 to generate the viral capsid proteins. However, when P1 is co-expressed with 3CD (vectors no. 1300+1310 and 1300+1315), the 98 kDa signal completely disappears and a new product is detected that corresponds in molecular weight to VP1 (33.5 kDa). This result shows that the viral protease is produced and highly active in the plant and that it recognizes and cleaves its co-produced substrate in the plant cells to generate EV71 capsid proteins.

The results obtained indicated that the level of VP1 accumulation in the plant is influenced by the ratio of *Agrobacterium* containing the P1 protein to *Agrobacterium* containing 3CD protease, with higher accumulation being obtained with a lower proportion of *Agrobacterium* containing 3CD protease (FIG. 2: compare 1300+1315 (4:2), 1300+1315 (4:1) and 1300+1315 (4:0.5)). The origin of 3CD, either HK08 vs GDFS08, also impacts on the accumulation level of VP1 in the plant (FIG. 2: 1300+1310 (4:0.5) vs 1300+1315 (4:0.5)). Finally, it was observed that the highest VP1 accumulation level was obtained from expression vectors comprising DNA amplification elements (FIG. 2: 1301+1311 (4:2)).

In the following experiment, P1 was maintained under the control of CPMV-HT+BeYDV (1301) while different 3CD expression cassettes were co-transformed at different dilutions at the time of infiltration. Western blot analysis using the anti-VP1 monoclonal antibody on crude protein extracts from the transformed plants indicated that VP1 accumulation was observed over a range of P1 to protease ratios and construct components. The vector combination resulting in the highest level of VP1 accumulation was 1301+1310, with a ratio of *Agrobacterium* strain concentration of 4:0.5 (structural protein:protease) in the bacterial suspension (FIG. 3).

Analysis of VLP Formation

The incorporation of VP1 into VLPs was evaluated with the use of size exclusion chromatography (SEC) of concentrated extracts. Colloidal particles were concentrated from crude clarified extracts by high-speed centrifugation (75 000×g for 20 min.). The pellet was washed and resuspended in ⅙ volume of resuspension buffer (50 mM PBS pH 7.4, 150 mM NaCl) and loaded onto a Sephacryl S-500 gel filtration column. The column was eluted with resuspension buffer and the elution fractions were characterized by SDS-PAGE and western blotting.

A protein extract from plants transiently transformed with 1301+1310 (4:0.5) was subjected to SEC separation and elution fractions were analyzed by Coomassie-stained SDS-PAGE and anti-VP1 western blot. The results presented in FIG. 4A show that most of the host proteins eluted from the column in the late fractions, peaking at fraction 16 while the VP1-specific signal was found in earlier fractions, peaking at fraction 12, where very little host protein is found. VP1 being a relatively small protein, it would be expected to elute from the column with the majority of the host proteins if not incorporated into high molecular weight structures. Hence, the elution profile observed for VP1 was strongly indicative that VP1 had been integrated into a high molecular weight structure. A combination of the western blot and the Coomassie-stained gel also suggested that the abundant protein identified by an arrow in the Coomassie-stained SDS-PAGE in FIG. 4A could be VP1.

A sample of elution fraction 12 from this experiment was sent to Institut Armand-Frappier (IAF, Laval, Québec) for analysis by transmission electron microscopy (TEM). The sample was examined after negative staining with 3% phosphotungstic acid. FIG. 4B shows that spherical particles of 30 nm identical in size and appearance to empty EV71 particles found in EV71-infected Vero cell cultures (Liu et al., PLoS ONE 6, e20005) are observed in elution fraction 12. This result indicates that the high molecular weight structures in which VP1 is incorporated are genuine EV71 VLPs.

Partial Purification

The VLP purification method of the VLPExpress screening platform was developed for the purification of enveloped VLPs (140 nm diameter) from transformed plant biomass. The method uses an enzymatic digestion of cell walls for the release of extracellular and cytosolic content and the extract obtained is subjected to deep filtration and to microfiltration before being centrifuged at 16 000 g for 6 h to pellet VLPs. The pellet is resuspended in 1/60 volume of resuspension solution (100 mM Na/KPO.sub.4 pH 7.4, 150 mM NaCl, 0.01% TWEEN-80) and sterile filtered (0.2 μm).

Figure 5:
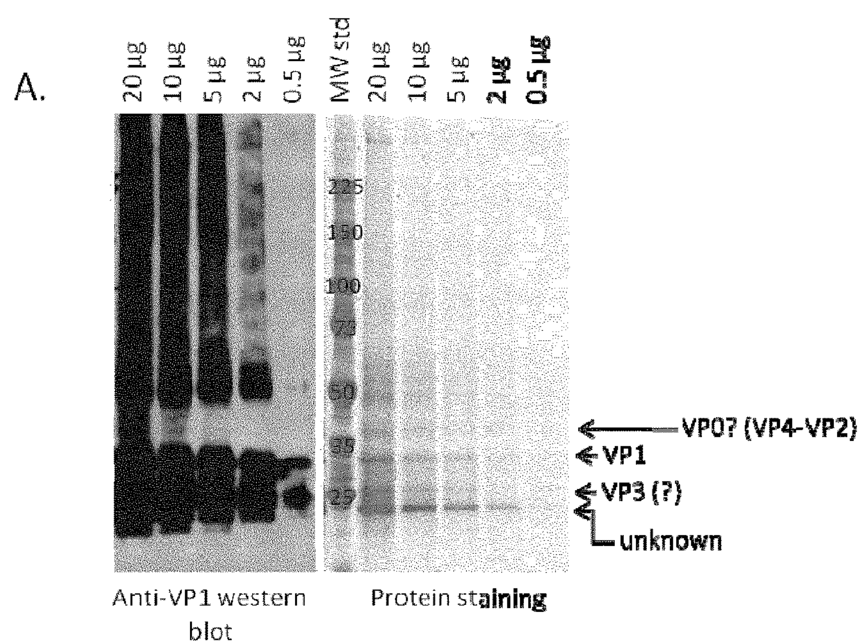
FIG. 5 shows the characterization of purified EV71 PVLPs. (A) Coomassie-stained SDS-PAGE and western blot analysis of purified EV71 PVLPs. The band corresponding to VP1 in the Coomassie-stained gel is indicated. Other bands, corresponding in molecular weight to other EV71 capsid proteins are also identified. (B) Negative staining transmission electron microscopic examination of purified EV71 PVLPs. The sample was diluted 1/100 prior to examination. The bar represents 100 nm.
Figure 5:
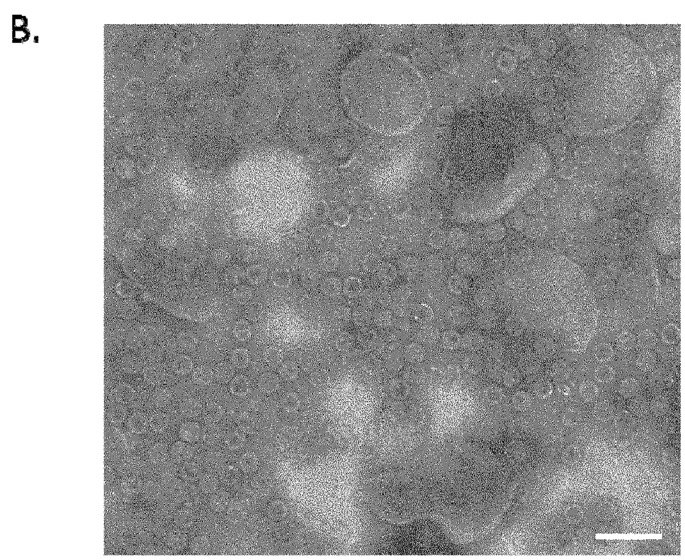

The VLPExpress® purification method was tested for its capacity to concentrate the 30 nm non-enveloped EV71 VLPs. The purification method was applied to plants transformed with expression vectors 1301+1310 (4:0.5). The resulting product was analyzed by Coomassie-stained SDS-PAGE and anti-VP1 western blot (FIG. 5A). Coomassie-stained SDS-PAGE analysis of the purification product showed the presence of proteins corresponding in molecular weight to EV71 coat proteins (indicated by arrows, FIG. 5A, right panel). The identity of VP1 was confirmed by western blot (FIG. 5A, left panel). For other capsid proteins, the identification was based on the estimated molecular weight; 37.5 kDa for VP0 and 26.5 kDa for VP3. VP4 and VP2 were expected to be found in the form of uncleaved VP0 since in the formation of viral particles the cleavage between VP4 and VP2 only occurs after the internalization of viral RNA. Transmission electron microscopic analysis of the purified product revealed abundant spherical structures of 30 nm, corresponding in size and shape to EV71 VLPs (FIG. 5B).

Conclusions on the Expression

The work performed to demonstrate the capacity of the plant-based transient expression platform to produce EV71 VLPs has led to the following conclusions:

- EV71 P1 and 3CD proteins are efficiently produced in the system
- 3CD is active in planta and correctly processes P1 into capsid proteins
- EV71 capsid proteins assemble into VLPs
- EV71 VLPs are extractable and can be purified intact from plant biomass.

Example 2 Expression Poliovirus Expression

Gene Synthesis

DNA segments encoding poliovirus (PV) structural protein P1 and protease 3CD from Human enterovirus C serotype PV-1 may be used. The candidate sequences for P1 and 3CD are available in GenBank. Non limiting examples of these sequences are:

For P1: amino acids sequence GenBank ID NP_041277 (amino acids 1-881) (SEQ ID NO:10); nucleotide sequence: GenBank ID NC_002058 (nucleotides 743-3385) (SEQ ID NO: 9);

For 3CD: amino acid sequence GenBank ID NP_041277 (amino acids 1566-2209) (SEQ ID NO:8); nucleotide sequence: GenBank ID NC_002058 (nucleotides 5438-7369) (SEQ ID NO:7).

Two P1 genes may be synthesized. The first may be produced using the wild-type sequence while the second may be based on an optimized sequence (human codon usage) determined using standard methods as known in the art. The 3CD gene may be synthesized based on its wild-type sequence. Both wild-type genes (P1 and 3CD) may be synthesized by Invitrogen™ (formerly GeneArt®) and the optimized P1 gene is optimized and synthesized by DNA2.0.

Molecular Cloning

The synthesized genes may be cloned into plant expression vectors. Selected vector components include transcription and translation regulatory elements from a cowpea mosaic virus (CPMV)-based cassette or an alfalfa plastocyanin gene, as both regulatory elements have previously been used with success for high expression of recombinant proteins. DNA amplification elements from the Bean yellow dwarf geminivirus (BeYDV) may also be integrated into the plant expression vectors. Each gene construct may therefore be cloned in expression vectors with or without DNA amplification elements. Table 2 presents the plant expression cassettes that may be assembled.

TABLE 2

Plant expression cassettes for the expression of PV structural polyprotein P1 and protease 3CD in *N. benthamiana*.

| Coding region | Regulatory element | DNA amplification elements |
|---|---|---|
| P1 (Wt) | CPMV HT | — |
| P1 (Wt) | CPMV HT | BeYDV + rep |
| P1 (Wt) | Plastocyanin | — |
| P1 (Wt) | Plastocyanin | BeYDV + rep |
| P1 (Opt) | CPMV HT | — |
| P1 (Opt) | CPMV HT | BeYDV + rep |
| P1 (Opt) | Plastocyanin | — |
| P1 (Opt) | Plastocyanin | BeYDV + rep |
| 3CD | CPMV HT | — |
| 3CD | CPMV HT | BeYDV + rep |
| 3CD | Plastocyanin | — |
| 3CD | Plastocyanin | BeYDV + rep |

Analysis of Expression—Selecting the Best Recombinant Gene Constructs

Each expression cassettes may be cloned into a plasmid vector that may then be transferred to *Agrobacterium tumefaciens*. Transient expression may be initiated by vacuum infiltration of the transgenic *Agrobacterium* inoculum that leads to transfer of mobile DNA copies of the DNA constructs into plant cells. Transient expression of multiple components (co-expression) may be performed by infiltration of mixes of *Agrobacterium* inoculums (co-infiltration). As one component being introduced into the plant is structural (P1), and the substrate of the second component, the 3CD protease, the level of expression of the two components may be modulated. This may be performed by using different promoters, DNA amplification systems of variable strength, by varying the relative abundance of each inoculum (P1 and 3CD) at the time of infiltration, or a combination thereof.

Expression vectors with P1 may be first screened for their ability to express P1 alone, and when combined with 3CD vectors, for their ability to produce high levels of proteolytic fragments. Accumulation of proteolytic fragments may be monitored through disappearance of unprocessed P1. Viral protease is shown to be produced and highly active in the plant, as well as being able to recognize and cleave its co-produced substrate in the plant cells to generate PV capsid proteins.

The level of proteolytic fragments accumulation in the plant may be influenced by the ratio of *Agrobacterium* containing the P1 protein to *Agrobacterium* containing 3CD protease, with higher accumulation being obtained with a lower proportion of *Agrobacterium* containing 3CD protease. Observation is made with respect to the presence of DNA amplification elements and the use of the different regulatory elements on the processing of P1 and the accumulation of proteolytic fragments.

Analysis of VLP Formation

The incorporation of VP1 into VLPs may be evaluated with the use of size exclusion chromatography (SEC) of concentrated extracts. Colloidal particles may be concentrated from crude clarified extracts by high-speed centrifugation. The pellet may be washed and resuspended in 1/6 volume of resuspension buffer and loaded onto a gel filtration column. The column may be eluted with resuspension buffer and the elution fractions are characterized by SDS-PAGE and western blotting.

A protein extract from plants transiently transformed may be subjected to SEC separation and elution fractions are analyzed by Coomassie-stained SDS-PAGE. The results may show that most of the host proteins eluted from the column in the late fractions, while the VP1-specific signal may be found in earlier fractions. VP1 being a relatively small protein, it would be expected to elute from the column with the majority of the host proteins if not incorporated into high molecular weight structures. Hence, the elution profile observed for VP1 may be strongly indicative that VP1 had been integrated into a high molecular weight structure. A combination of the western blot and the Coomassie-stained gel may also suggested that the abundant protein observed in the Coomassie-stained SDS-PAGE could be VP1.

A sample from this experiment may be sent to Institut Armand-Frappier (IAF, Laval, Québec) for analysis by transmission electron microscopy (TEM). The result indicates that the high molecular weight structures in which VP1 is incorporated are genuine PV VLPs.

Partial Purification

The VLP purification method of the VLPExpress screening platform was developed for the purification of enveloped VLPs (140 nm diameter) from transformed plant biomass. The method uses an enzymatic digestion of cell walls for the release of extracellular and cytosolic content and the extract obtained is subjected to deep filtration and to microfiltration before being centrifuged to pellet VLPs. The pellet is resuspended in resuspension solution and sterile filtered.

The VLPExpress purification method may be tested for its capacity to concentrate the non-enveloped PV VLPs. Coomassie-stained SDS-PAGE analysis of the purification product may show the presence of proteins corresponding in molecular weight to PV coat proteins. Identification of the capsid proteins may be based on their estimated molecular weight.

Example 3 Purification

Protein extraction was performed using either mechanical extraction technique, or enzymatic degradation of the cell wall as described in WO 2011/035422 and PCT/CA2012/050180 (which are incorporated herein by reference). Enzymatic extraction is advantageous over mechanical extraction in that it results in an increased release of product with minimal release of contaminating plant proteins, with the major contaminants in the resulting extract being the enzymes used for cell wall disruption, which can be removed using adequate subsequent downstream steps.

Mechanical or enzymatic extracts were submitted to centrifugation to eliminate cellular debris, Agrobacteria, DNA and larger particles. Centrifuged extracts were then passed through filtration steps performed in order to remove solids in suspension, reduce bioburden, and stabilize and condition the extract prior to downstream processing. Although recovery of EV71 VLPs in the filtrate could not be evaluated in absence of a quantification assay, Western blot analyses indicated that VLP loss during filtration steps was minimal. The resulting clarified extract was further processed using tangential flow filtration (TFF) or directly loaded onto chromatographic media as suitable.

The size of VLPs enables the use of TFF for efficient and selective elimination of the soluble proteins found in the clarified extract, including enzymes used for cell wall depolymerisation. The TFF step also concentrates VLPs and enables a buffer exchange in preparation for chromatography.

Several chromatography approaches (anion exchange, cation exchange, hydrophobic interaction chromatography (HIC) and pseudo-affinity), modes (bind or flow through) and buffer conditions (pH 5 to 8, conductivity from 10 to 80 mS/cm) were evaluated for their capacity to increase purity and reduce contaminating DNA and endotoxins, while preserving the desired characteristics of a VLP. We have found that under certain conditions, the POROS® D (a weak anion exchange resin) used in flow through mode could provide the most efficient removal of DNA and endotoxins from concentrated EV71 VLPs.

A second TFF step was added following chromatography in the EV71 VLP purification process. The role of this TFF step was to concentrate and formulate the product in the desired buffer. Pore size and operating conditions for this second TFF step were determined based on parameters identified for the first TFF. Finally, a drug substance with concentrated apparently pure EV71 particles was obtained following 0.22-μm filtration. The product was formulated in PBS containing 0.01% Polysorbate 80.

VLP Characterization

A first lot of EV71 VLPs was produced with the adapted process described above (lot no. 479-23-018) and the product was fully characterized (Table 3, lot no. 479-23-018). Purity was determined by densitometry from scans of Coomassie stained gels where only bands that showed positive signals on Western blots (anti VP1-VP2), and that could be further confirmed by mass spectrometry, were considered as part of product. Product quality profile analysis indicated that the preparation contained highly pure EV71 VLPs.

TABLE 3

Quality attributes of EV71 VLP, lot no. 479-23-018.

| Attribute | EV71 VLPs Initial process |
|---|---|
| Lot number | 479-23-018 |
| Purity | 96.4% |
| Protein conc. (BCA, μg/ml) | 1192.4 |

TABLE 3-continued

Quality attributes of EV71 VLP, lot no. 479-23-018.

| Attribute | EV71 VLPs Initial process |
|---|---|
| SEC-HPLC (% in void volume (high molecular weight structures) | 100% |
| Light scattering Particle size (nm) | 48.3 |
| Electron microscopy | Round particles Approx. 30 nm Well dispersed |
| Tryptic mapping/MS Number of impurities detected ($p < 0.05$ and >2 peptides) 3 first impurities | 2 Ubiquitin (4 pep) Peroxidase (2 pep) |
| Bioburden (CFU//ml) | <10 |

* Preliminary estimates calculated from a single run.

Figure 6:
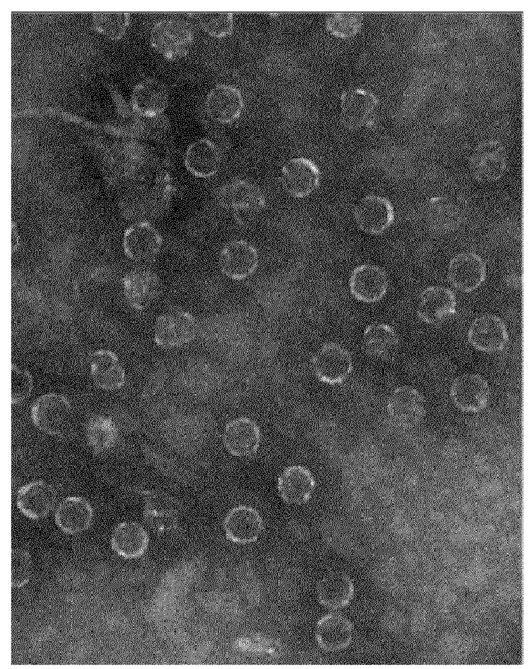
FIG. 6 shows characterization of lot 479-23-018 by electron microscopy.
Figure 7:
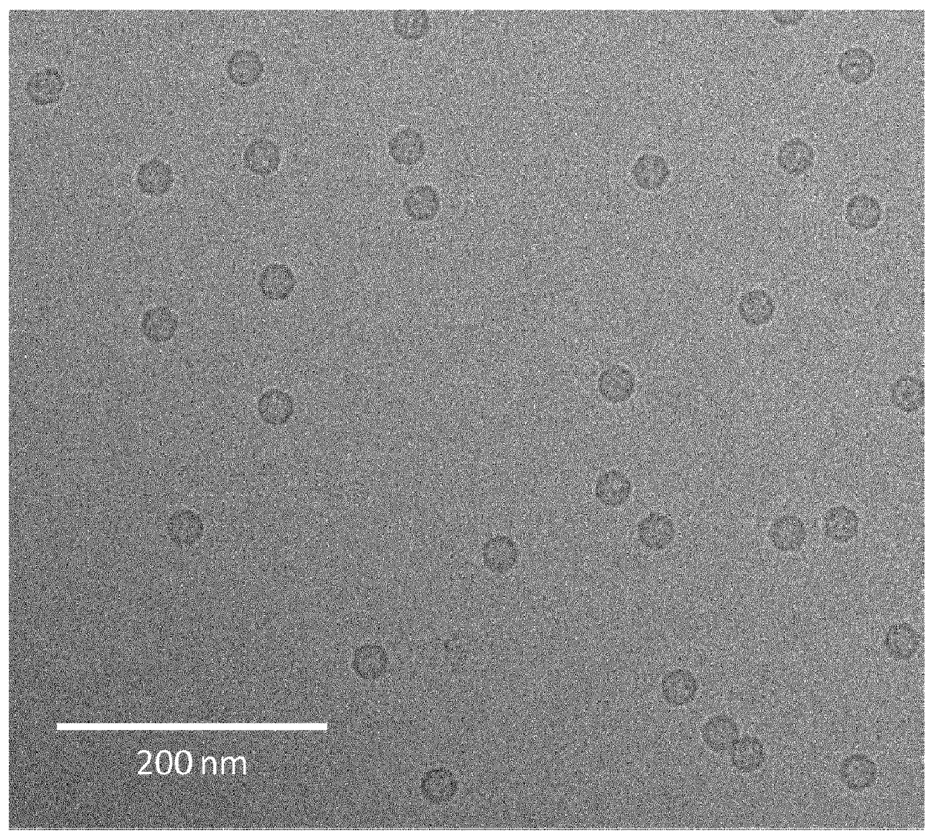
FIG. 7 shows cryo-electron microscopy analysis of EV71 PVLPs extracted by enzyme-assisted method, processes and selected by HIC (lot no. 479-31-020).

Further analysis of the product by electron microscopy confirmed that purified EV71 VLPs were intact (FIG. 6A) and tryptic mapping by mass spectrometry confirmed the purity of the product.

Example 4 Process Modifications

Purification of VLPs with Intact VP1 by HIC

During initial screening of chromatographic approaches to purify EV71 VLPs, it had been noticed that HIC resins could separate the VLPs containing intact VP1 from particles containing fragmented VP1. Under certain conditions, while the particles containing LMW VP1 fragments were strongly bound to the resins, the intact particles were flowing through the column. This HIC step was therefore inserted as a polishing step following POROS® D chromatography. EV71 particles purified through this process were homogenous in size (light scattering), at close to 100% purity, with no protein contaminants detectable by mass spectrometry. Product quality attributes of this product (lot no. 479-31-020) are presented in table 3, central column. Modified extraction procedure.

Plant extract may be clarified by acidification at pH around 5.2 or by heat treatment and the coagulate eliminated by centrifugation. The heat treatment was inserted between the mechanical extraction and centrifugation steps. Using a heat treatment of 10 minutes at 60° C. (pH 8.0) eliminated more than 90% of soluble proteins without affecting the solubility of EV71 VLPs to a detectable level. The VP1 remained intact when extracted and clarified under these conditions.

Figure 8:
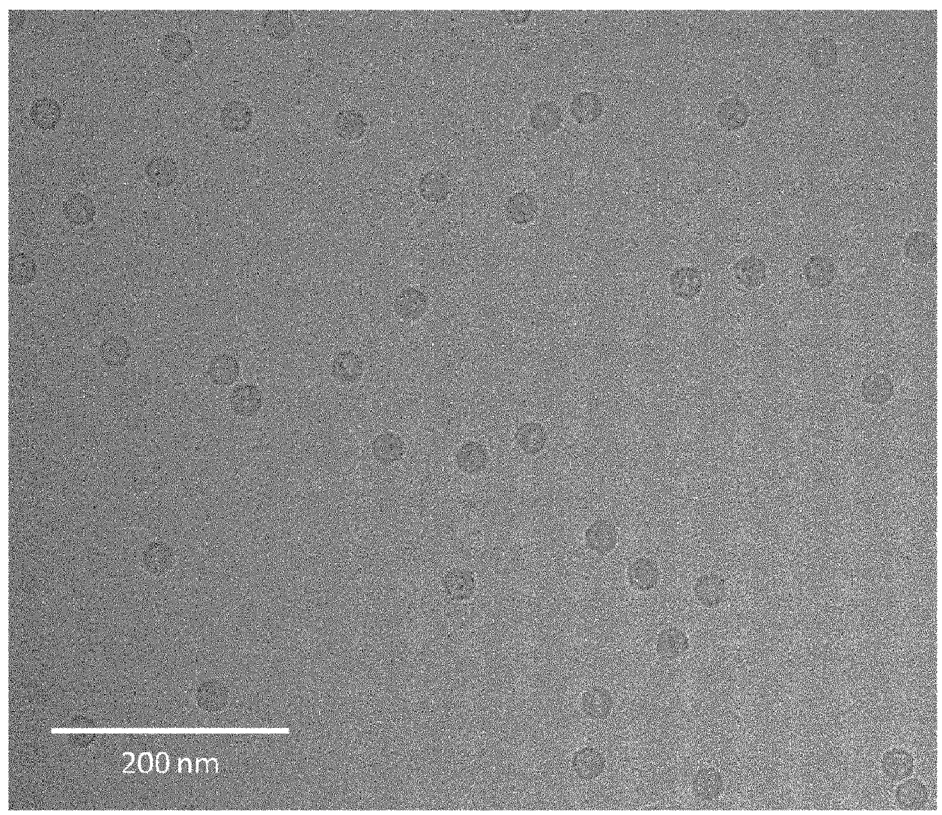
FIG. 8 shows cryo-electron microscopy analysis of EV71 PVLPs extracted by mechanical extraction method (pH 8.0) with heat treatment (lot no. 479-32-020).

The mechanical extraction at pH 8.0, combined with heat treatment-based clarification, was implemented for EV71 VLP purification process in replacement of the enzymatic extraction. A VLP lot has been produced with this process (lot no. 479-32-020). The characteristic of the product are presented in table 4 (third column). The results obtained showed that mechanical extraction, used in conjunction with heat-based clarification of proteins, represents an efficient primary recovery step that is fully compatible with the previously defined downstream steps. The resulting process is high yielding and generates an EV71 VLP product that is 98% pure. Light scattering profiles of the EV71 VLPs prepared from this process showed high homogeneity. Cryo TEM analysis of this product confirmed that the particles have the size and shape of EV71 VLPs (FIG. 8).

TABLE 4

Comparison of EV71 VLP characteristics for lots produced with processes comprising enzymatic extraction with and without HIC or mechanical extraction.

| Attribute | Enzymatic extraction (pH 5.1) without HIC | Enzymatic extraction (pH 5.1) with HIC | Mechanical extraction (pH 8.0) with heat treatment |
|---|---|---|---|
| Lot number | 479-35-020 | 479-31-020 | 479-32-020 |
| Purity | 95.5% | 100% | 98.2% |
| Protein conc. (BCA, µg/ml) | 352.8 | 297.8 | 715.3 |
| SEC-HPLC (% in void volume (high molecular weight structures) | 100% | 98.9% | 100% |
| Electron microscopy | To be determined | Round particles 25-30 nm Well dispersed | Round particles 25-30 nm Well dispersed |

* Preliminary estimates calculated from a single run for each process.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A method of producing an Enterovirus-like particle (EVLP) in a plant, portion of a plant or plant cell comprising:

a) introducing into the plant, portion of the plant, or plant cell a first nucleic acid comprising a first regulatory region active in the plant operatively linked to a nucleotide sequence encoding an Enterovirus polyprotein, wherein the Enterovirus polyprotein consists of Enterovirus 71 polyprotein P1;

b) introducing a second nucleic acid comprising a second regulatory region active in the plant and operatively linked to a second nucleotide sequence encoding one or more Enterovirus 71 3C or 3CD protease into the plant, portion of the plant, or plant cell; and c) incubating the plant, portion of the plant, or plant cell under conditions that permit expression of the first and second nucleic acid to produce the Enterovirus 71 polyprotein P1 and the one or more Enterovirus 71 3C or 3CD protease, the Enterovirus 71 polyprotein P1 being processed into structural proteins VP1, VP3, and VP0 or VP1, VP2, VP3 and VP4, thereby producing the EVLP.

2. The method of claim 1, wherein the ratio of introduced amounts of the first nucleic acid relative to the second nucleic acid is between 20:1 and 0.5:1.

3. The method of claim 1, wherein the Enterovirus polyprotein comprises structural proteins VP1, VP2, VP3, VP4, or a combination thereof.

4. The method of claim 1, wherein in the step of introducing (step a), the nucleic acid is transiently expressed in the plant.

5. The method of claim 1, wherein, in the step of introducing (step a), the nucleic acid is stably expressed in the plant.

6. A method of producing an Enterovirus like particle (EVLP) in a plant, portion of a plant or plant cell comprising:

a) providing the plant, portion of the plant or plant cell comprising a first nucleic acid comprising a first regulatory region active in the plant operatively linked to a first nucleotide sequence encoding an Enterovirus polyprotein wherein the Enterovirus polyprotein consist of Enterovirus 71 polyprotein P1 and a second nucleic acid comprising a second regulatory region active in the plant operatively linked to a second nucleotide sequence encoding one or more Enterovirus 71 3C or 3CD protease;

b) incubating the plant, portion of the plant or plant cell under conditions that permit expression of the nucleic acids to produce the Enterovirus 71 polyprotein P1 and the one or more Enterovirus 71 3C or 3CD protease, the Enterovirus 71 polyprotein P1 being processed into structural proteins VP1, VP3, and VP0 or VP1, VP2, VP3 and VP4, thereby producing the EVLP.

7. The method of claim 1, wherein the first nucleic acid sequence comprises the first regulatory region operatively linked to one or more comovirus enhancer, the nucleotide sequence encoding the Enterovirus polyprotein, and one or more amplification element, and further comprising the step of:

introducing a third nucleic acid encoding a replicase into the plant, portion of the plant, or plant cell.

8. The method of claim 1, wherein the second nucleic acid does not comprise one or more amplification element or one or more comovirus enhancer.

9. The method of claim 6, wherein the ratio of the first nucleic acid relative to the second nucleic acid is between 20:1 and 0.5:1.

10. The method of claim 6, wherein the first nucleic acid sequence comprises the first regulatory region operatively linked to one or more comovirus enhancer, the nucleotide sequence encoding the Enterovirus polyprotein, and one or more amplification element, and further comprising the step of:

introducing a third nucleic acid encoding a replicase into the plant, portion of the plant, or plant cell.

11. The method of claim 6, wherein the second nucleic acid does not comprise one or more amplification element or one or more comovirus enhancer.

12. The method of claim 1, further comprising the step(s) of:

(d) harvesting the plant, portion of the plant, or plant cell; and/or (e) purifying the EVLP.

13. The method of claim 6, further comprising the step(s) of:

(d) harvesting the plant, portion of the plant, or plant cell; and/or (e) purifying the EVLP.

14. The method of claim 1, wherein the first nucleic acid and the second nucleic acid are on separate nucleic acid constructs.

15. The method of claim 6, wherein the first nucleic acid and the second nucleic acid are on separate nucleic acid constructs.

16. The method of claim 1, wherein the first nucleic acid and the second nucleic acid are on the same nucleic acid construct.

17. The method of claim 6, wherein the first nucleic acid and the second nucleic acid are on the same nucleic acid construct.

* * * * *

SEQUENCE LISTING

```
<160> NUMBER OF SEQ ID NOS: 10

<210> SEQ ID NO 1
<211> LENGTH: 645
<212> TYPE: PRT
<213> ORGANISM: Enterovirus A71

<400> SEQUENCE: 1

Gly Pro Ser Leu Asp Phe Ala Leu Ser Leu Leu Arg Arg Asn Val Arg
1               5                   10                  15

Gln Val Gln Thr Asp Gln Gly His Phe Thr Met Leu Gly Val Arg Asp
            20                  25                  30

Arg Leu Ala Val Leu Pro Arg His Ser Gln Pro Gly Lys Thr Ile Trp
        35                  40                  45

Ile Glu His Lys Leu Val Asn Val Leu Asp Ala Val Glu Leu Val Asp
    50                  55                  60
```

-continued

```
Glu Gln Gly Val Asn Leu Glu Leu Thr Leu Ile Thr Leu Asp Thr Asn
65                  70                  75                  80

Glu Lys Phe Arg Asp Ile Thr Lys Phe Ile Pro Glu Asn Ile Ser Ala
                85                  90                  95

Ala Ser Asp Ala Thr Leu Val Ile Asn Thr Glu His Met Pro Ser Met
            100                 105                 110

Phe Val Pro Val Gly Asp Val Val Gln Tyr Gly Phe Leu Asn Leu Ser
        115                 120                 125

Gly Lys Pro Thr His Arg Thr Met Met Tyr Asn Phe Pro Thr Lys Ala
    130                 135                 140

Gly Gln Cys Gly Gly Val Val Thr Ser Val Gly Lys Ile Ile Gly Ile
145                 150                 155                 160

His Ile Gly Gly Asn Gly Arg Gln Gly Phe Cys Ala Gly Leu Lys Arg
                165                 170                 175

Ser Tyr Phe Ala Ser Glu Gln Gly Glu Ile Gln Trp Val Lys Pro Asn
            180                 185                 190

Lys Glu Thr Gly Arg Leu Asn Ile Asn Gly Pro Thr Arg Thr Lys Leu
        195                 200                 205

Glu Pro Ser Val Phe His Asp Ile Phe Glu Gly Asn Lys Glu Pro Ala
    210                 215                 220

Val Leu His Ser Lys Asp Pro Arg Leu Glu Val Asp Phe Glu Gln Ala
225                 230                 235                 240

Leu Phe Ser Lys Tyr Val Gly Asn Thr Leu Tyr Glu Pro Asp Glu Tyr
                245                 250                 255

Ile Lys Glu Ala Ala Leu His Tyr Ala Asn Gln Leu Lys Gln Leu Glu
            260                 265                 270

Ile Asn Thr Ser Gln Met Ser Met Glu Glu Ala Cys Tyr Gly Thr Glu
        275                 280                 285

Asn Leu Glu Ala Ile Asp Leu His Thr Ser Ala Gly Tyr Pro Tyr Ser
    290                 295                 300

Ala Leu Gly Ile Lys Lys Arg Asp Ile Leu Asp Pro Thr Thr Arg Asp
305                 310                 315                 320

Val Ser Lys Met Lys Phe Tyr Met Asp Lys Tyr Gly Leu Asp Leu Pro
                325                 330                 335

Tyr Ser Thr Tyr Val Lys Asp Glu Leu Arg Ser Ile Asp Lys Ile Lys
            340                 345                 350

Lys Gly Lys Ser Arg Leu Ile Glu Ala Ser Ser Leu Asn Asp Ser Val
        355                 360                 365

Tyr Leu Arg Met Ala Phe Gly His Leu Tyr Glu Ala Phe His Ala Asn
    370                 375                 380

Pro Gly Thr Ile Thr Gly Ser Ala Val Gly Cys Asn Pro Asp Thr Phe
385                 390                 395                 400

Trp Ser Lys Leu Pro Ile Leu Leu Pro Gly Ser Leu Phe Ala Phe Asp
                405                 410                 415

Tyr Ser Gly Tyr Asp Ala Ser Leu Ser Pro Val Trp Phe Arg Ala Leu
            420                 425                 430

Glu Leu Val Leu Arg Glu Ile Gly Tyr Ser Glu Gly Ala Val Ser Leu
        435                 440                 445

Ile Glu Gly Ile Asn His Thr His His Val Tyr Arg Asn Lys Thr Tyr
    450                 455                 460

Cys Val Leu Gly Gly Met Pro Ser Gly Cys Ser Gly Thr Ser Ile Phe
465                 470                 475                 480
```

```
Asn Ser Met Ile Asn Asn Ile Ile Ile Arg Ala Leu Leu Ile Lys Thr
                485                 490                 495

Phe Lys Gly Ile Asp Leu Asp Glu Leu Asn Met Val Ala Tyr Gly Asp
            500                 505                 510

Asp Val Leu Ala Ser Tyr Pro Phe Pro Ile Asp Cys Leu Glu Leu Ala
        515                 520                 525

Lys Thr Gly Lys Glu Tyr Gly Leu Thr Met Thr Pro Ala Asp Lys Ser
    530                 535                 540

Pro Cys Phe Asn Glu Val Asn Trp Gly Asn Ala Thr Phe Leu Lys Arg
545                 550                 555                 560

Gly Phe Leu Pro Asp Glu Gln Phe Pro Phe Leu Ile His Pro Thr Met
                565                 570                 575

Pro Met Arg Glu Ile His Glu Ser Ile Arg Trp Thr Lys Asp Ala Arg
            580                 585                 590

Asn Thr Gln Asp His Val Arg Ser Leu Cys Leu Leu Ala Trp His Asn
        595                 600                 605

Gly Lys Gln Glu Tyr Glu Lys Phe Val Ser Thr Ile Arg Ser Val Pro
    610                 615                 620

Val Gly Arg Ala Leu Ala Ile Pro Asn Tyr Glu Asn Leu Arg Arg Asn
625                 630                 635                 640

Trp Leu Glu Leu Phe
                645


<210> SEQ ID NO 2
<211> LENGTH: 1935
<212> TYPE: DNA
<213> ORGANISM: Enterovirus A71

<400> SEQUENCE: 2

ggcccgagcc ttgattttgc cctctcccta ctgaggagga acgtcaggca agtccaaaca      60

gaccaggggc atttcaccat gttgggtgtt agggatcgct tagcagtcct cccacgccac     120

tcacaacccg gcaaaactat ttggattgag cacaaactcg tgaacgtcct tgatgcagtt     180

gaattggtgg atgagcaagg agtcaacctg gagttaaccc tcatcactct tgacactaac     240

gaaaagttta gggatatcac caaattcatc ccagaaaata ttagtgctgc cagtgatgcc     300

accctagtga tcaacacgga gcacatgccc tcaatgtttg tcccggtggg tgacgttgtg     360

cagtatggct tcttgaacct cagtggcaag cctacccatc gcaccatgat gtacaacttt     420

cctactaaag caggacagtg tgggggagtg gtgacatctg ttgggaagat tatcggtatt     480

cacattggtg gcaatggcag acaaggtttt tgcgcaggcc tcaaaaggag ttactttgct     540

agtgaacaag gagagatcca gtgggttaag cccaataaag aaactggaag actcaacatc     600

aatggaccaa cccgcaccaa gctagaaccc agtgtattcc atgatatctt tgagggaaat     660

aaggagccag ctgtcttgca cagtaaagac ccccgacttg aggtagattt tgaacaggcc     720

ctgttctcta agtatgtggg gaatacacta tatgagcctg acgagtacat caaagaggca     780

gctcttcatt atgcaaacca attaaagcag ctagaaatca acacctctca aatgagcatg     840

gaggaggcct gctacggtac tgagaatctt gaggctattg atcttcatac tagtgcaggt     900

taccccctata gtgccctggg gataaagaaa agagacatct tagaccctac caccagggac     960

gtgagtaaaa tgaagttcta catggacaaa tatggtcttg atctccctta ctccacttat    1020

gtcaaggacg agctgcgctc aattgataaa attaagaaag ggaagtcccg tctgattgag    1080

gccagtagtt taaatgattc agtgtacctt agaatggctt tcggtcattt gtatgaggct    1140
```

```
ttccacgcaa atcctgggac tataactgga tcagccgtgg ggtgtaaccc tgacacattc   1200

tggagcaagc tgccaatttt gctccctggt tcactctttg cctttgacta ctcaggttat   1260

gatgctagcc ttagccctgt ctggttcaga gcattagaat tggtccttag ggagataggg   1320

tatagtgaag ggcagtctc actcattgag ggaatcaacc acacacacca tgtgtatcgt    1380

aataagacct attgtgtgct tggtgggatg ccctcaggct gctcgggaac atccattttc   1440

aactcaatga tcaacaacat tattatcaga gcactgctca taaaaacatt taagggcatt   1500

gatttggatg aactcaacat ggtcgcttat ggagatgatg tgctcgctag ctaccccttc   1560

ccaattgatt gcttggagtt agcgaagact ggcaaggagt atggtctaac catgacccct   1620

gcggataagt ctccttgctt taatgaagtt aattggggta atgcgacctt tctcaagagg   1680

ggctttttac ccgatgaaca gtttccattt ttgatccacc ccactatgcc aatgagggag   1740

atccatgagt ccattcgatg gaccaaggat gcacgaaaca ctcaagatca tgtgcggtcc   1800

ttgtgcctcc tagcatggca taatggtaag caagaatatg agaaatttgt gagtacaatt   1860

aggtctgtcc cagtgggaag agcgttggct atcccaaatt atgaaaacct tagacgtaat   1920

tggctcgagt tattt                                                    1935
```

<210> SEQ ID NO 3
<211> LENGTH: 645
<212> TYPE: PRT
<213> ORGANISM: Enterovirus A71

<400> SEQUENCE: 3

```
Gly Pro Ser Leu Asp Phe Ala Leu Ser Leu Leu Arg Arg Asn Ile Arg
1               5                   10                  15

Gln Val Gln Thr Asp Gln Gly His Phe Thr Met Leu Gly Val Arg Asp
            20                  25                  30

Arg Leu Ala Val Leu Pro Arg His Ser Gln Pro Gly Lys Thr Ile Trp
        35                  40                  45

Ile Glu His Lys Leu Val Asn Ile Leu Asp Ala Val Glu Leu Val Asp
    50                  55                  60

Glu Gln Gly Val Asn Leu Glu Leu Thr Leu Ile Thr Leu Asp Thr Asn
65                  70                  75                  80

Glu Lys Phe Arg Asp Ile Thr Lys Phe Ile Pro Glu Ser Ile Ser Thr
                85                  90                  95

Ala Ser Asp Ala Thr Leu Val Ile Asn Thr Glu His Met Pro Ser Met
            100                 105                 110

Phe Val Pro Val Gly Asp Val Val Gln Tyr Gly Phe Leu Asn Leu Ser
        115                 120                 125

Gly Lys Pro Thr His Arg Thr Met Met Tyr Asn Phe Pro Thr Lys Ala
    130                 135                 140

Gly Gln Cys Gly Gly Val Val Thr Ser Val Gly Lys Val Ile Gly Ile
145                 150                 155                 160

His Ile Gly Gly Asn Gly Arg Gln Gly Phe Cys Ala Gly Leu Lys Arg
                165                 170                 175

Ser Tyr Phe Ala Ser Glu Gln Gly Glu Ile Gln Trp Val Lys Pro Asn
            180                 185                 190

Lys Glu Thr Gly Arg Leu Asn Ile Asn Gly Pro Thr Arg Thr Lys Leu
        195                 200                 205

Glu Pro Ser Val Phe His Asp Val Phe Glu Gly Asn Lys Glu Pro Ala
    210                 215                 220

Val Leu His Gly Lys Asp Pro Arg Leu Glu Val Asp Phe Glu Gln Ala
```

-continued

```
225                 230                 235                 240

Leu Phe Ser Lys Tyr Val Gly Asn Thr Leu Tyr Glu Pro Asp Glu Tyr
                245                 250                 255

Ile Lys Glu Ala Ala Leu His Tyr Ala Asn Gln Leu Lys Gln Leu Glu
            260                 265                 270

Ile Asn Thr Ser Gln Met Ser Met Glu Glu Ala Cys Tyr Gly Thr Glu
        275                 280                 285

Asn Leu Glu Ala Ile Asp Leu His Thr Ser Ala Gly Tyr Pro Tyr Ser
    290                 295                 300

Ala Leu Gly Ile Lys Lys Arg Asp Ile Leu Asp Pro Thr Thr Arg Asp
305                 310                 315                 320

Val Ser Lys Met Lys Ser Tyr Met Asp Lys Tyr Gly Leu Asp Leu Pro
                325                 330                 335

Tyr Ser Thr Tyr Val Lys Asp Glu Leu Arg Ser Ile Asp Lys Ile Lys
            340                 345                 350

Lys Gly Lys Ser Arg Leu Ile Glu Ala Ser Ser Leu Asn Asp Ser Val
        355                 360                 365

Tyr Leu Arg Met Thr Phe Gly His Leu Tyr Glu Ala Phe His Ala Asn
    370                 375                 380

Pro Gly Thr Ile Thr Gly Ser Ala Val Gly Cys Asn Pro Asp Thr Phe
385                 390                 395                 400

Trp Ser Lys Leu Pro Ile Leu Leu Pro Gly Ser Leu Phe Ala Phe Asp
                405                 410                 415

Tyr Ser Gly Tyr Asp Ala Ser Leu Ser Pro Val Trp Phe Arg Ala Leu
            420                 425                 430

Glu Met Val Leu Arg Glu Ile Gly Tyr Ser Glu Glu Ala Val Ser Leu
        435                 440                 445

Ile Glu Gly Ile Asn His Thr His His Val Tyr Arg Asn Lys Thr Tyr
    450                 455                 460

Cys Val Leu Gly Gly Met Pro Ser Gly Cys Ser Gly Thr Ser Ile Phe
465                 470                 475                 480

Asn Ser Met Ile Asn Asn Ile Ile Ile Arg Ala Leu Leu Ile Lys Thr
                485                 490                 495

Phe Lys Gly Ile Asp Leu Asp Glu Leu Asn Met Val Ala Tyr Gly Asp
            500                 505                 510

Asp Val Leu Ala Ser Tyr Pro Phe Pro Ile Asp Cys Leu Glu Leu Ala
        515                 520                 525

Lys Thr Gly Lys Glu Tyr Gly Leu Thr Met Thr Pro Ala Asp Lys Ser
    530                 535                 540

Pro Cys Phe Asn Glu Val Asn Trp Gly Asn Ala Thr Phe Leu Lys Arg
545                 550                 555                 560

Gly Phe Leu Pro Asp Glu Gln Phe Pro Phe Leu Ile His Pro Thr Met
                565                 570                 575

Pro Met Arg Glu Ile His Glu Ser Ile Arg Trp Thr Lys Asp Ala Arg
            580                 585                 590

Asn Thr Gln Asp His Val Arg Ser Leu Cys Leu Leu Ala Trp His Asn
        595                 600                 605

Gly Lys Gln Glu Tyr Glu Lys Phe Val Ser Thr Ile Arg Ser Val Pro
    610                 615                 620

Ile Gly Arg Ala Leu Ala Ile Pro Asn Tyr Glu Asn Leu Arg Arg Asn
625                 630                 635                 640

Trp Leu Glu Leu Phe
                645
```

<210> SEQ ID NO 4
<211> LENGTH: 1935
<212> TYPE: DNA
<213> ORGANISM: Enterovirus A71

<400> SEQUENCE: 4

```
ggcccgagtc ttgattttgc tctctccctg ttaaggagga acatcaggca agtccaaaca     60
gaccaggggc atttcaccat gttgggtgtt agggatcgtt tagcagtcct cccacgtcac    120
tcacaacccg gcaaaactat ttggatcgaa cacaaactcg tgaacattct tgatgcagtt    180
gaattggtgg atgagcaagg agtcaacctg gaattgaccc tcatcactct tgacactaac    240
gaaaagttta gggatatcac caaattcatc ccagaaagta ttagcactgc cagtgatgcc    300
accctagtga tcaacacgga gcacatgccc tcaatgtttg tcccggtggg tgacgtcgtg    360
cagtatggct ttttgaatct tagtggcaag cccacccatc gcaccatgat gtacaacttt    420
cctactaaag cgggacagtg tggaggagta gtgacatctg ttgggaaagt catcggtatt    480
cacattggtg gcaatggtag acaaggtttt tgcgcaggcc tcaaaaggag ttactttgct    540
agtgaacaag gggagatcca gtgggttaag cccaataaag aaactggaag actcaacatc    600
aatggaccaa cccgcaccaa gttggaaccc agtgtattcc atgatgtctt cgagggaaat    660
aaggaaccag ctgtcttgca cggcaaagat ccccgactcg aggtagattt tgagcaggcc    720
ctgttctcta agtatgtggg aaacacgcta tatgagcctg acgagtacat caaagaggca    780
gctcttcatt atgcaaatca attaaagcaa ctagaaatta atacctccca gatgagcatg    840
gaggaagcct gctatggtac tgagaatctt gaggctatcg atcttcatac tagtgcaggt    900
taccccctata gtgccctggg aataaagaaa agagacatct tagaccctac caccagggac    960
gtgagtaaaa tgaaatccta tatggacaaa tatggtctcg atctccctta ctccacttat   1020
gtcaaggatg agctgcgctc aattgataaa attaagaaag ggaagtcccg tctgatcgag   1080
gccagcagtt taaatgattc agtgtacctc agaatgactt tcggtcattt gtatgaggct   1140
ttccacgcaa atcctgggac gataactgga tcagccgtgg ggtgtaaccc tgacacattc   1200
tggagcaagc tgccaatctt gcttcctggt tcactctttg cctttgacta ctcaggttat   1260
gatgctagcc ttagccctgt ctggttcaga gcattagaaa tggtccttag ggagataggg   1320
tatagtgaag aggcggtctc actcattgag ggaatcaacc acacacacca cgtgtatcgt   1380
aacaagacct attgtgtgct tggtgggatg ccctcaggct gttcgggaac atccatcttc   1440
aactcaatga tcaacaacat tattatcaga gcactgctca taaaaacatt taagggcatt   1500
gatttggatg aactcaacat ggtcgcttat ggggatgatg tgcttgctag ctacccctto   1560
ccaatcgatt gcttggagtt agcaaagact ggcaaggagt atggtctgac catgactcct   1620
gcagataagt ccccttgctt taatgaagtt aattggggta atgcgacctt cctcaagagg   1680
ggctttttac ctgatgagca gtttccattt ttgatccacc ctactatgcc aatgcgggag   1740
atccatgaat ccattcgatg gactaaggac gcacgaaaca ctcaagatca tgtacggtcc   1800
ttgtgcctcc tagcatggca taatggtaag caagaatatg aaaaatttgt gagcacaatt   1860
aggtctgtcc caataggaag agctttggct atcccaaatt atgaaaatct tagacgcaat   1920
tggctcgagt tattt                                                      1935
```

<210> SEQ ID NO 5
<211> LENGTH: 862
<212> TYPE: PRT

```
<213> ORGANISM: Enterovirus A71

<400> SEQUENCE: 5

Met Gly Ser Gln Val Ser Thr Gln Arg Ser Gly Ser His Glu Asn Ser
1               5                   10                  15

Asn Ser Ala Thr Glu Gly Ser Thr Ile Asn Tyr Thr Thr Ile Asn Tyr
            20                  25                  30

Tyr Lys Asp Ser Tyr Ala Ala Thr Ala Gly Lys Gln Ser Leu Lys Gln
        35                  40                  45

Asp Pro Asp Lys Phe Ala Asn Pro Val Lys Asp Ile Phe Thr Glu Met
    50                  55                  60

Ala Ala Pro Leu Lys Ser Pro Ser Ala Glu Ala Cys Gly Tyr Ser Asp
65                  70                  75                  80

Arg Val Ala Gln Leu Thr Ile Gly Asn Ser Thr Ile Thr Thr Gln Glu
                85                  90                  95

Ala Ala Asn Ile Ile Val Gly Tyr Gly Glu Trp Pro Ser Tyr Cys Ser
            100                 105                 110

Asp Ser Asp Ala Thr Ala Val Asp Lys Pro Thr Arg Pro Asp Val Ser
        115                 120                 125

Val Asn Arg Phe Tyr Thr Leu Asp Thr Lys Leu Trp Glu Lys Ser Ser
    130                 135                 140

Lys Gly Trp Tyr Trp Lys Phe Pro Asp Val Leu Thr Glu Thr Gly Val
145                 150                 155                 160

Phe Gly Gln Asn Ala Gln Phe His Tyr Leu Tyr Arg Ser Gly Phe Cys
                165                 170                 175

Ile His Val Gln Cys Asn Ala Ser Lys Phe His Gln Gly Ala Leu Leu
            180                 185                 190

Val Ala Val Leu Pro Glu Tyr Val Ile Gly Thr Val Ala Gly Gly Thr
        195                 200                 205

Gly Thr Glu Asp Ser His Pro Pro Tyr Lys Gln Thr Gln Pro Gly Ala
    210                 215                 220

Asp Gly Phe Glu Leu Gln His Pro Tyr Val Leu Asp Ala Gly Ile Pro
225                 230                 235                 240

Ile Ser Gln Leu Thr Val Cys Pro His Gln Trp Ile Asn Leu Arg Thr
                245                 250                 255

Asn Asn Cys Ala Thr Ile Ile Val Pro Tyr Ile Asn Ala Leu Pro Phe
            260                 265                 270

Asp Ser Ala Leu Asn His Cys Asn Phe Gly Leu Leu Val Val Pro Ile
        275                 280                 285

Ser Pro Leu Asp Tyr Asp Gln Gly Ala Thr Pro Val Ile Pro Ile Thr
    290                 295                 300

Ile Thr Leu Ala Pro Met Cys Ser Glu Phe Ala Gly Leu Arg Gln Ala
305                 310                 315                 320

Val Thr Gln Gly Phe Pro Thr Glu Leu Lys Pro Gly Thr Asn Gln Phe
                325                 330                 335

Leu Thr Thr Asp Asp Gly Val Ser Ala Pro Ile Leu Pro Asn Phe His
            340                 345                 350

Pro Thr Pro Cys Ile His Ile Pro Gly Glu Val Arg Asn Leu Leu Glu
        355                 360                 365

Leu Cys Gln Val Glu Thr Ile Leu Glu Val Asn Asn Val Pro Thr Asn
    370                 375                 380

Ala Thr Ser Leu Met Glu Arg Leu Arg Phe Pro Val Ser Ala Gln Ala
385                 390                 395                 400
```

```
Gly Lys Gly Glu Leu Cys Ala Val Phe Arg Ala Asp Pro Gly Arg Asn
                405                 410                 415

Gly Pro Trp Gln Ser Thr Leu Leu Gly Gln Leu Cys Gly Tyr Tyr Thr
            420                 425                 430

Gln Trp Ser Gly Ser Leu Glu Val Thr Phe Met Phe Thr Gly Ser Phe
        435                 440                 445

Met Ala Thr Gly Lys Met Leu Ile Ala Tyr Thr Pro Pro Gly Gly Pro
    450                 455                 460

Leu Pro Lys Asp Arg Ala Thr Ala Met Leu Gly Thr His Val Ile Trp
465                 470                 475                 480

Asp Phe Gly Leu Gln Ser Ser Val Thr Leu Val Ile Pro Trp Ile Ser
                485                 490                 495

Asn Thr His Tyr Arg Ala His Ala Arg Asp Gly Val Phe Asp Tyr Tyr
            500                 505                 510

Thr Thr Gly Leu Val Ser Ile Trp Tyr Gln Thr Asn Tyr Val Val Pro
        515                 520                 525

Ile Gly Ala Pro Asn Thr Ala Tyr Ile Ile Ala Leu Ala Ala Ala Gln
    530                 535                 540

Lys Asn Phe Thr Met Lys Leu Cys Lys Asp Ala Ser Asp Ile Leu Gln
545                 550                 555                 560

Thr Gly Thr Ile Gln Gly Asp Arg Val Ala Asp Val Ile Glu Ser Ser
                565                 570                 575

Ile Gly Asp Ser Val Ser Arg Ala Leu Thr Gln Ala Leu Pro Ala Pro
            580                 585                 590

Thr Gly Gln Asn Thr Gln Val Ser Ser His Arg Leu Asp Thr Gly Lys
        595                 600                 605

Val Pro Ala Leu Gln Ala Ala Glu Ile Gly Ala Ser Ser Asn Ala Ser
    610                 615                 620

Asp Glu Ser Met Ile Glu Thr Arg Cys Val Leu Asn Ser His Ser Thr
625                 630                 635                 640

Ala Glu Thr Thr Leu Asp Ser Phe Phe Ser Arg Ala Gly Leu Val Gly
                645                 650                 655

Glu Ile Asp Leu Pro Leu Glu Gly Thr Thr Asn Pro Asn Gly Tyr Ala
            660                 665                 670

Asn Trp Asp Ile Asp Ile Thr Gly Tyr Ala Gln Met Arg Arg Lys Val
        675                 680                 685

Glu Leu Phe Thr Tyr Met Arg Phe Asp Ala Glu Phe Thr Phe Val Ala
    690                 695                 700

Cys Thr Pro Thr Gly Glu Val Val Pro Gln Leu Leu Gln Tyr Met Phe
705                 710                 715                 720

Val Pro Pro Gly Ala Pro Lys Pro Asp Ser Arg Glu Ser Leu Ala Trp
                725                 730                 735

Gln Thr Ala Thr Asn Pro Ser Val Phe Val Lys Leu Ser Asp Pro Pro
            740                 745                 750

Ala Gln Val Ser Val Pro Phe Met Ser Pro Ala Ser Ala Tyr Gln Trp
        755                 760                 765

Phe Tyr Asp Gly Tyr Pro Thr Phe Gly Glu His Lys Gln Glu Lys Asp
    770                 775                 780

Leu Glu Tyr Gly Ala Cys Pro Asn Asn Met Met Gly Thr Phe Ser Val
785                 790                 795                 800

Arg Thr Val Gly Thr Ser Lys Ser Lys Tyr Pro Leu Val Val Arg Ile
                805                 810                 815

Tyr Met Arg Met Lys His Val Arg Ala Trp Ile Pro Arg Pro Met Arg
```

```
            820                 825                 830

Asn Gln Asn Tyr Leu Phe Lys Ala Asn Pro Asn Tyr Ala Gly Asn Ser
        835                 840                 845

Ile Lys Pro Thr Gly Thr Ser Arg Thr Ala Ile Thr Thr Leu
    850                 855                 860


<210> SEQ ID NO 6
<211> LENGTH: 2586
<212> TYPE: DNA
<213> ORGANISM: Enterovirus A71

<400> SEQUENCE: 6

atgggttcgc aggtgtccac gcagcgctcc ggttctcatg aaaattcaaa ctcagccacc     60

gagggttcca ccataaacta caccaccatt aattattaca aagactccta tgctgccaca    120

gcaggcaaac agagtctcaa gcaggatcca gacaagtttg caaatcctgt taaagacatc    180

ttcactgaaa tggcagcgcc actgaagtcc ccatccgctg aggcatgtgg atacagtgat    240

cgagtagcgc aattaactat tggtaactcc accatcacca cgcaagaagc ggctaacatc    300

atagttggtt atggtgagtg gccttcctac tgctcggatt ctgacgctac agcagtggat    360

aagccaacgc gcccggatgt ttcagtgaac aggttttata cattggacac taaattgtgg    420

gagaaatcgt ccaagggatg gtactggaaa ttcccggatg tgttaactga aactggggtt    480

tttgggcaaa atgcacaatt ccactacctc taccgatcag ggttctgtat ccacgtgcag    540

tgcaatgcta gtaaattcca ccaaggagca ctcctagtcg ctgttctacc agagtacgtc    600

attgggacag tggcaggcgg cacagggacg gaagatagtc acccccctta caagcagact    660

caacccggcg ccgatggctt cgaattgcaa cacccgtacg tgcttgatgc tggcatccca    720

atatcacagt taacagtgtg cccacatcag tggattaatt tgagaaccaa caattgtgct    780

acaataatag tgccatacat taacgcactg ccttttgatt ccgccttgaa ccactgcaat    840

tttggcctat tagttgtgcc tattagccca ctagattacg accaaggagc gacgccagta    900

atccctataa ctatcacatt agccccaatg tgttctgaat tcgcaggtct taggcaggca    960

gtcacgcaag gatttcccac cgagttgaaa cctggcacaa atcaattttt aaccactgat   1020

gatggcgttt cagcacctat tctaccaaac ttccacccca ccccgtgtat ccatatacct   1080

ggtgaagtta ggaacttgct agagttatgc caggtggaaa ccattctaga ggttaacaat   1140

gtgcccacga atgccactag tttaatggag agactgcgct ttccagtctc agcacaagca   1200

gggaaaggtg agctgtgtgc ggtgttcaga gctgatcctg ggcgaaatgg gccgtggcag   1260

tccaccttgc tgggtcagtt gtgtgggtat tacacccaat ggtcaggatc attggaagtc   1320

accttcatgt ttactggatc ctttatggct accggcaaga tgctcatagc ctatacaccg   1380

ccaggaggcc ctttgcccaa ggaccgggcg accgccatgt tgggcacgca cgtcatctgg   1440

gattttgggc tgcaatcgtc cgttaccctt gtaataccat ggatcagcaa cactcactac   1500

agagcgcatg cccgagatgg agtgtttgac tactacacca cagggttagt cagtatatgg   1560

tatcagacaa attacgtggt tccaattggg gcgcctaata cagcctatat aatagcacta   1620

gcggcagccc aaaagaattt cactatgaag ttgtgcaagg atgctagtga tatcctacaa   1680

acgggcacca tccagggaga tagggtagca gatgtaattg aaagttccat aggggatagc   1740

gtgagcagag ccctcactca agctctacca gcacccacag gccagaacac acaggtgagc   1800

agtcatcgac tggatacagg caaggttcca gcactccaag ctgctgaaat tggagcatca   1860

tcaaatgcta gtgacgagag catgatcgag acacgctgtg ttcttaactc gcacagcaca   1920
```

```
gctgagacca ctcttgatag tttcttcagc agagcgggat tagttggaga gatagatctt   1980
cctcttgaag gcacaactaa cccaaatggt tatgccaact gggacataga tataacaggt   2040
tacgcacaaa tgcgcagaaa ggtggagtta ttcacctaca tgcgctttga tgcagagttc   2100
actttcgttg cgtgcacacc taccggggaa gttgtcccac aattgctcca atatatgttt   2160
gtaccacctg gagcccctaa gccagactcc agggagtccc tcgcatggca aaccgccacc   2220
aacccctcag tttttgtcaa gttgtcagac cctccagcac aggtttcagt accattcatg   2280
tcacccgcga gtgcttacca atggttctat gacggatatc ccacattcgg ggaacacaaa   2340
caggagaaag atcttgagta tggggcgtgc cctaataaca tgatgggtac gttctcagtg   2400
cggactgtag ggacttccaa atccaagtat cctttagtgg ttaggattta catgaggatg   2460
aagcacgtca gggcgtggat acctcgcccg atgcgtaacc aaaactacct attcaaggcc   2520
aacccaaatt atgctggcaa ctccattaag ccaactggta ctagtcgcac agcgatcact   2580
actctt                                                              2586
```

```
<210> SEQ ID NO 7
<211> LENGTH: 1932
<212> TYPE: DNA
<213> ORGANISM: Enterovirus C

<400> SEQUENCE: 7

ggaccagggt tcgattacgc agtggctatg gctaaaagaa acattgttac agcaactact     60
agcaagggag agttcactat gttaggagtc cacgacaacg tggctatttt accaacccac    120
gcttcacctg gtgaaagcat tgtgatcgat ggcaaagaag tggagatctt ggatgccaaa    180
gcgctcgaag atcaagcagg aaccaatctt gaaatcacta taatcactct aaagagaaat    240
gaaaagttca gagacattag accacatata cctactcaaa tcactgagac aaatgatgga    300
gtcttgatcg tgaacactag caagtacccc aatatgtatg ttcctgtcgg tgctgtgact    360
gaacagggat atctaaatct cggtgggcgc caaactgctc gtactctaat gtacaacttt    420
ccaaccagag caggacagtg tggtggagtc atcacatgta ctgggaaagt catcgggatg    480
catgttggtg ggaacggttc acacgggttt gcagcggccc tgaagcgatc atacttcact    540
cagagtcaag gtgaaatcca gtggatgaga ccttcgaagg aagtgggata tccaatcata    600
aatgccccgt ccaaaaccaa gcttgaaccc agtgctttcc actatgtgtt tgaaggggtg    660
aaggaaccag cagtcctcac taaaaacgat cccaggctta agacagactt tgaggaggca    720
attttctcca agtacgtggg taacaaaatt actgaagtgg atgagtacat gaaagaggca    780
gtagaccact atgctggcca gctcatgtca ctagacatca acacagaaca aatgtgcttg    840
gaggatgcca tgtatggcac tgatggtcta gaagcacttg atttgtccac cagtgctggc    900
taccccttatg tagcaatggg aaagaagaag agagacatct tgaacaaaca aaccagagac    960
actaaggaaa tgcaaaaact gctcgacaca tatggaatca acctcccact ggtgacttat   1020
gtaaaggatg aacttagatc caaaacaaag gttgagcagg ggaaatccag attaattgaa   1080
gcttctagtt tgaatgactc agtggcaatg agaatggctt ttgggaacct atatgctgct   1140
tttcacaaaa acccaggagt gataacaggt tcagcagtgg ggtgcgatcc agatttgttt   1200
tggagcaaaa ttccggtatt gatggaagag aagctgtttg cttttgacta cacagggtat   1260
gatgcatctc tcagccctgc ttggttcgag gcactaaaga tggtgcttga gaaaatcgga   1320
ttcggagaca gagttgacta catcgactac ctaaaccact cacaccacct gtacaagaat   1380
```

```
aaaacatact gtgtcaaggg cggtatgcca tctggctgct caggcacttc aatttttaac   1440

tcaatgatta acaacttgat tatcaggaca ctcttactga aaacctacaa gggcatagat   1500

ttagaccacc taaaaatgat tgcctatggt gatgatgtaa ttgcttccta cccccatgaa   1560

gttgacgcta gtctcctagc ccaatcagga aaagactatg gactaactat gactccagct   1620

gacaaatcag ctacatttga aacagtcaca tgggagaatg taacattctt gaagagattc   1680

ttcagggcag acgagaaata cccatttctt attcatccag taatgccaat gaaggaaatt   1740

catgaatcaa ttagatggac taaagatcct aggaacactc aggatcacgt tcgctctctg   1800

tgccttttag cttggcacaa tggcgaagaa gaatataaca aattcctagc taaaatcagg   1860

agtgtgccaa ttggaagagc tttattgctc ccagagtact caacattgta ccgccgttgg   1920

cttgactcat tt                                                       1932
```

<210> SEQ ID NO 8
<211> LENGTH: 644
<212> TYPE: PRT
<213> ORGANISM: Enterovirus C

<400> SEQUENCE: 8

```
Gly Pro Gly Phe Asp Tyr Ala Val Ala Met Ala Lys Arg Asn Ile Val
1               5                   10                  15

Thr Ala Thr Thr Ser Lys Gly Glu Phe Thr Met Leu Gly Val His Asp
            20                  25                  30

Asn Val Ala Ile Leu Pro Thr His Ala Ser Pro Gly Glu Ser Ile Val
        35                  40                  45

Ile Asp Gly Lys Glu Val Glu Ile Leu Asp Ala Lys Ala Leu Glu Asp
    50                  55                  60

Gln Ala Gly Thr Asn Leu Glu Ile Thr Ile Ile Thr Leu Lys Arg Asn
65                  70                  75                  80

Glu Lys Phe Arg Asp Ile Arg Pro His Ile Pro Thr Gln Ile Thr Glu
                85                  90                  95

Thr Asn Asp Gly Val Leu Ile Val Asn Thr Ser Lys Tyr Pro Asn Met
            100                 105                 110

Tyr Val Pro Val Gly Ala Val Thr Glu Gln Gly Tyr Leu Asn Leu Gly
        115                 120                 125

Gly Arg Gln Thr Ala Arg Thr Leu Met Tyr Asn Phe Pro Thr Arg Ala
    130                 135                 140

Gly Gln Cys Gly Gly Val Ile Thr Cys Thr Gly Lys Val Ile Gly Met
145                 150                 155                 160

His Val Gly Gly Asn Gly Ser His Gly Phe Ala Ala Ala Leu Lys Arg
                165                 170                 175

Ser Tyr Phe Thr Gln Ser Gln Gly Glu Ile Gln Trp Met Arg Pro Ser
            180                 185                 190

Lys Glu Val Gly Tyr Pro Ile Ile Asn Ala Pro Ser Lys Thr Lys Leu
        195                 200                 205

Glu Pro Ser Ala Phe His Tyr Val Phe Glu Gly Val Lys Glu Pro Ala
    210                 215                 220

Val Leu Thr Lys Asn Asp Pro Arg Leu Lys Thr Asp Phe Glu Glu Ala
225                 230                 235                 240

Ile Phe Ser Lys Tyr Val Gly Asn Lys Ile Thr Glu Val Asp Glu Tyr
                245                 250                 255

Met Lys Glu Ala Val Asp His Tyr Ala Gly Gln Leu Met Ser Leu Asp
            260                 265                 270
```

```
Ile Asn Thr Glu Gln Met Cys Leu Glu Asp Ala Met Tyr Gly Thr Asp
        275                 280                 285

Gly Leu Glu Ala Leu Asp Leu Ser Thr Ser Ala Gly Tyr Pro Tyr Val
    290                 295                 300

Ala Met Gly Lys Lys Lys Arg Asp Ile Leu Asn Lys Gln Thr Arg Asp
305                 310                 315                 320

Thr Lys Glu Met Gln Lys Leu Leu Asp Thr Tyr Gly Ile Asn Leu Pro
                325                 330                 335

Leu Val Thr Tyr Val Lys Asp Glu Leu Arg Ser Lys Thr Lys Val Glu
            340                 345                 350

Gln Gly Lys Ser Arg Leu Ile Glu Ala Ser Ser Leu Asn Asp Ser Val
        355                 360                 365

Ala Met Arg Met Ala Phe Gly Asn Leu Tyr Ala Ala Phe His Lys Asn
    370                 375                 380

Pro Gly Val Ile Thr Gly Ser Ala Val Gly Cys Asp Pro Asp Leu Phe
385                 390                 395                 400

Trp Ser Lys Ile Pro Val Leu Met Glu Glu Lys Leu Phe Ala Phe Asp
                405                 410                 415

Tyr Thr Gly Tyr Asp Ala Ser Leu Ser Pro Ala Trp Phe Glu Ala Leu
            420                 425                 430

Lys Met Val Leu Glu Lys Ile Gly Phe Gly Asp Arg Val Asp Tyr Ile
        435                 440                 445

Asp Tyr Leu Asn His Ser His His Leu Tyr Lys Asn Lys Thr Tyr Cys
    450                 455                 460

Val Lys Gly Gly Met Pro Ser Gly Cys Ser Gly Thr Ser Ile Phe Asn
465                 470                 475                 480

Ser Met Ile Asn Asn Leu Ile Ile Arg Thr Leu Leu Leu Lys Thr Tyr
                485                 490                 495

Lys Gly Ile Asp Leu Asp His Leu Lys Met Ile Ala Tyr Gly Asp Asp
            500                 505                 510

Val Ile Ala Ser Tyr Pro His Glu Val Asp Ala Ser Leu Leu Ala Gln
        515                 520                 525

Ser Gly Lys Asp Tyr Gly Leu Thr Met Thr Pro Ala Asp Lys Ser Ala
    530                 535                 540

Thr Phe Glu Thr Val Thr Trp Glu Asn Val Thr Phe Leu Lys Arg Phe
545                 550                 555                 560

Phe Arg Ala Asp Glu Lys Tyr Pro Phe Leu Ile His Pro Val Met Pro
                565                 570                 575

Met Lys Glu Ile His Glu Ser Ile Arg Trp Thr Lys Asp Pro Arg Asn
            580                 585                 590

Thr Gln Asp His Val Arg Ser Leu Cys Leu Leu Ala Trp His Asn Gly
        595                 600                 605

Glu Glu Glu Tyr Asn Lys Phe Leu Ala Lys Ile Arg Ser Val Pro Ile
    610                 615                 620

Gly Arg Ala Leu Leu Leu Pro Glu Tyr Ser Thr Leu Tyr Arg Arg Trp
625                 630                 635                 640

Leu Asp Ser Phe
```

<210> SEQ ID NO 9
<211> LENGTH: 2643
<212> TYPE: DNA
<213> ORGANISM: Enterovirus C

<400> SEQUENCE: 9

-continued

```
atgggtgctc aggtttcatc acagaaagtg ggcgcacatg aaaactcaaa tagagcgtat     60
ggtggttcta ccattaatta caccaccatt aattattata gagattcagc tagtaacgcg    120
gcttcgaaac aggacttctc tcaagaccct tccaagttca ccgagcccat caaggatgtc    180
ctgataaaaa cagccccaat gctaaactcg ccaaacatag aggcttgcgg gtatagcgat    240
agagtactgc aattaacact gggaaactcc actataacca cacaggaggc ggctaattca    300
gtagtcgctt atgggcgttg gcctgaatat ctgagggaca gcgaagccaa tccagtggac    360
cagccgacag aaccagacgt cgctgcatgc aggttttata cgctagacac cgtgtcttgg    420
acgaaagagt cgcgagggtg gtggtggaag ttgcctgatg cactgaggga catgggactc    480
tttgggcaaa atatgtacta ccactaccta ggtaggtccg ggtacaccgt gcatgtacag    540
tgtaacgcct ccaaattcca ccagggggca ctaggggtat tcgccgtacc agagatgtgt    600
ctggccgggg atagcaacac cactaccatg cacaccagct atcaaaatgc caatcctggc    660
gagaaaggag gcactttcac gggtacgttc actcctgaca acaaccagac atcacctgcc    720
cgcaggttct gcccggtgga ttacctcctt ggaaatggca cgttgttggg gaatgccttt    780
gtgttcccgc accagataat aaacctacgg accaacaact gtgctacact ggtactccct    840
tacgtgaact ccctctcgat agatagtatg gtaaagcaca ataattgggg aattgcaata    900
ttaccattgg ccccattaaa ttttgctagt gagtcctccc cagagattcc aatcaccttg    960
accatagccc ctatgtgctg tgagttcaat ggattaagaa acatcaccct gccacgctta   1020
cagggcctgc cggtcatgaa cacccctggt agcaatcaat atcttactgc agacaacttc   1080
cagtcaccgt gtgcgctgcc tgaatttgat gtgaccccac ctattgacat acccggtgaa   1140
gtaaagaaca tgatggaatt ggcagaaatc gacaccatga ttccctttga cttaagtgcc   1200
acaaaaaaga acaccatgga aatgtatagg gttcggttaa gtgacaaacc acatacagac   1260
gatcccatac tctgcctgtc actctctcca gcttcagatc ctaggttgtc acatactatg   1320
cttggagaaa tcctaaatta ctacacacac tgggcaggat ccctgaagtt cacgtttctg   1380
ttctgtggat tcatgatggc aactggcaaa ctgttggtgt catacgcgcc tcctggagcc   1440
gacccaccaa agaagcgtaa ggaggcgatg ttgggaacac atgtgatctg ggacatagga   1500
ctgcagtcct catgtactat ggtagtgcca tggattagca acaccacgta tcggcaaacc   1560
atagatgata gtttcaccga aggcggatac atcagcgtct tctaccaaac tagaatagtc   1620
gtccctcttt cgacacccag agagatggac atccttggtt ttgtgtcagc gtgtaatgac   1680
ttcagcgtgc gcttgttgcg agataccaca catatagagc aaaaagcgct agcacagggg   1740
ttaggtcaga tgcttgaaag catgattgac aacacagtcc gtgaaacggt gggggcggca   1800
acatctagag acgctctccc aaacactgaa gccagtggac caacacactc caaggaaatt   1860
ccggcactca ccgcagtgga aactggggcc acaaatccac tagtcccttc tgatacagtg   1920
caaaccagac atgttgtaca acataggtca aggtcagagt ctagcataga gtctttcttc   1980
gcgcggggtg catgcgtgac cattatgacc gtggataacc cagcttccac cacgaataag   2040
gataagctat ttgcagtgtg gaagatcact tataaagata ctgtccagtt acggaggaaa   2100
ttggagttct tcacctattc tagatttgat atggaactta cctttgtggt tactgcaaat   2160
ttcactgaga ctaacaatgg gcatgcctta aatcaagtgt accaaattat gtacgtacca   2220
ccaggcgctc cagtgcccga gaaatgggac gactacacat ggcaaacctc atcaaatcca   2280
tcaatctttt acacctacgg aacagctcca gcccggatct cggtaccgta tgttggtatt   2340
tcgaacgcct attcacactt ttacgacggt tttccaaagg taccactgaa ggaccagtcg   2400
```

```
gcagcactag gtgactccct ttatggtgca gcatctctaa atgacttcgg tattttggct   2460

gttagagtag tcaatgatca caacccgacc aaggtcacct ccaaaatcag agtgtatcta   2520

aaacccaaac acatcagagt ctggtgcccg cgtccaccga gggcagtggc gtactacggc   2580

cctggagtgg attacaagga tggtacgctt acacccctct ccaccaagga tctgaccaca   2640

tat                                                                 2643


<210> SEQ ID NO 10
<211> LENGTH: 881
<212> TYPE: PRT
<213> ORGANISM: Enterovirus C

<400> SEQUENCE: 10

Met Gly Ala Gln Val Ser Ser Gln Lys Val Gly Ala His Glu Asn Ser
1               5                   10                  15

Asn Arg Ala Tyr Gly Gly Ser Thr Ile Asn Tyr Thr Thr Ile Asn Tyr
            20                  25                  30

Tyr Arg Asp Ser Ala Ser Asn Ala Ala Ser Lys Gln Asp Phe Ser Gln
        35                  40                  45

Asp Pro Ser Lys Phe Thr Glu Pro Ile Lys Asp Val Leu Ile Lys Thr
    50                  55                  60

Ala Pro Met Leu Asn Ser Pro Asn Ile Glu Ala Cys Gly Tyr Ser Asp
65                  70                  75                  80

Arg Val Leu Gln Leu Thr Leu Gly Asn Ser Thr Ile Thr Thr Gln Glu
                85                  90                  95

Ala Ala Asn Ser Val Val Ala Tyr Gly Arg Trp Pro Glu Tyr Leu Arg
            100                 105                 110

Asp Ser Glu Ala Asn Pro Val Asp Gln Pro Thr Glu Pro Asp Val Ala
        115                 120                 125

Ala Cys Arg Phe Tyr Thr Leu Asp Thr Val Ser Trp Thr Lys Glu Ser
    130                 135                 140

Arg Gly Trp Trp Trp Lys Leu Pro Asp Ala Leu Arg Asp Met Gly Leu
145                 150                 155                 160

Phe Gly Gln Asn Met Tyr Tyr His Tyr Leu Gly Arg Ser Gly Tyr Thr
                165                 170                 175

Val His Val Gln Cys Asn Ala Ser Lys Phe His Gln Gly Ala Leu Gly
            180                 185                 190

Val Phe Ala Val Pro Glu Met Cys Leu Ala Gly Asp Ser Asn Thr Thr
        195                 200                 205

Thr Met His Thr Ser Tyr Gln Asn Ala Asn Pro Gly Glu Lys Gly Gly
    210                 215                 220

Thr Phe Thr Gly Thr Phe Thr Pro Asp Asn Asn Gln Thr Ser Pro Ala
225                 230                 235                 240

Arg Arg Phe Cys Pro Val Asp Tyr Leu Leu Gly Asn Gly Thr Leu Leu
                245                 250                 255

Gly Asn Ala Phe Val Phe Pro His Gln Ile Ile Asn Leu Arg Thr Asn
            260                 265                 270

Asn Cys Ala Thr Leu Val Leu Pro Tyr Val Asn Ser Leu Ser Ile Asp
        275                 280                 285

Ser Met Val Lys His Asn Asn Trp Gly Ile Ala Ile Leu Pro Leu Ala
    290                 295                 300

Pro Leu Asn Phe Ala Ser Glu Ser Ser Pro Glu Ile Pro Ile Thr Leu
305                 310                 315                 320
```

-continued

```
Thr Ile Ala Pro Met Cys Cys Glu Phe Asn Gly Leu Arg Asn Ile Thr
                325                 330                 335

Leu Pro Arg Leu Gln Gly Leu Pro Val Met Asn Thr Pro Gly Ser Asn
            340                 345                 350

Gln Tyr Leu Thr Ala Asp Asn Phe Gln Ser Pro Cys Ala Leu Pro Glu
        355                 360                 365

Phe Asp Val Thr Pro Pro Ile Asp Ile Pro Gly Glu Val Lys Asn Met
    370                 375                 380

Met Glu Leu Ala Glu Ile Asp Thr Met Ile Pro Phe Asp Leu Ser Ala
385                 390                 395                 400

Thr Lys Lys Asn Thr Met Glu Met Tyr Arg Val Arg Leu Ser Asp Lys
                405                 410                 415

Pro His Thr Asp Asp Pro Ile Leu Cys Leu Ser Leu Ser Pro Ala Ser
            420                 425                 430

Asp Pro Arg Leu Ser His Thr Met Leu Gly Glu Ile Leu Asn Tyr Tyr
        435                 440                 445

Thr His Trp Ala Gly Ser Leu Lys Phe Thr Phe Leu Phe Cys Gly Phe
    450                 455                 460

Met Met Ala Thr Gly Lys Leu Leu Val Ser Tyr Ala Pro Pro Gly Ala
465                 470                 475                 480

Asp Pro Pro Lys Lys Arg Lys Glu Ala Met Leu Gly Thr His Val Ile
                485                 490                 495

Trp Asp Ile Gly Leu Gln Ser Ser Cys Thr Met Val Val Pro Trp Ile
            500                 505                 510

Ser Asn Thr Thr Tyr Arg Gln Thr Ile Asp Asp Ser Phe Thr Glu Gly
        515                 520                 525

Gly Tyr Ile Ser Val Phe Tyr Gln Thr Arg Ile Val Val Pro Leu Ser
    530                 535                 540

Thr Pro Arg Glu Met Asp Ile Leu Gly Phe Val Ser Ala Cys Asn Asp
545                 550                 555                 560

Phe Ser Val Arg Leu Leu Arg Asp Thr Thr His Ile Glu Gln Lys Ala
                565                 570                 575

Leu Ala Gln Gly Leu Gly Gln Met Leu Glu Ser Met Ile Asp Asn Thr
            580                 585                 590

Val Arg Glu Thr Val Gly Ala Ala Thr Ser Arg Asp Ala Leu Pro Asn
        595                 600                 605

Thr Glu Ala Ser Gly Pro Thr His Ser Lys Glu Ile Pro Ala Leu Thr
    610                 615                 620

Ala Val Glu Thr Gly Ala Thr Asn Pro Leu Val Pro Ser Asp Thr Val
625                 630                 635                 640

Gln Thr Arg His Val Val Gln His Arg Ser Arg Ser Glu Ser Ser Ile
                645                 650                 655

Glu Ser Phe Phe Ala Arg Gly Ala Cys Val Thr Ile Met Thr Val Asp
            660                 665                 670

Asn Pro Ala Ser Thr Thr Asn Lys Asp Lys Leu Phe Ala Val Trp Lys
        675                 680                 685

Ile Thr Tyr Lys Asp Thr Val Gln Leu Arg Arg Lys Leu Glu Phe Phe
    690                 695                 700

Thr Tyr Ser Arg Phe Asp Met Glu Leu Thr Phe Val Val Thr Ala Asn
705                 710                 715                 720

Phe Thr Glu Thr Asn Asn Gly His Ala Leu Asn Gln Val Tyr Gln Ile
                725                 730                 735

Met Tyr Val Pro Pro Gly Ala Pro Val Pro Glu Lys Trp Asp Asp Tyr
```

-continued

```
            740                 745                 750

Thr Trp Gln Thr Ser Ser Asn Pro Ser Ile Phe Tyr Thr Tyr Gly Thr
        755                 760                 765

Ala Pro Ala Arg Ile Ser Val Pro Tyr Val Gly Ile Ser Asn Ala Tyr
    770                 775                 780

Ser His Phe Tyr Asp Gly Phe Ser Lys Val Pro Leu Lys Asp Gln Ser
785                 790                 795                 800

Ala Ala Leu Gly Asp Ser Leu Tyr Gly Ala Ala Ser Leu Asn Asp Phe
                805                 810                 815

Gly Ile Leu Ala Val Arg Val Val Asn Asp His Asn Pro Thr Lys Val
            820                 825                 830

Thr Ser Lys Ile Arg Val Tyr Leu Lys Pro Lys His Ile Arg Val Trp
        835                 840                 845

Cys Pro Arg Pro Pro Arg Ala Val Ala Tyr Tyr Gly Pro Gly Val Asp
    850                 855                 860

Tyr Lys Asp Gly Thr Leu Thr Pro Leu Ser Thr Lys Asp Leu Thr Thr
865                 870                 875                 880

Tyr
```